United States Patent [19]
Gehret

[11] Patent Number: 4,978,677
[45] Date of Patent: Dec. 18, 1990

[54] C(29)-CARBONYLOXYMILBEMYCIN DERIVATIVES FOR CONTROLLING PARASITIC PETS OF ANIMALS AND PLANTS

[75] Inventor: Jean-Claude Gehret, Aesch, Switzerland

[73] Assignee: Ciba-Geigy Corporation, Ardsley, N.Y.

[21] Appl. No.: 432,297

[22] Filed: Nov. 6, 1989

Related U.S. Application Data

[63] Continuation of Ser. No. 22,198, Mar. 5, 1987, abandoned.

[30] Foreign Application Priority Data

Mar. 6, 1986 [CH] Switzerland ............................ 918/86

[51] Int. Cl.⁵ .................... A61K 31/365; C07D 493/22
[52] U.S. Cl. ..................................... 514/450; 549/264; 536/7.1
[58] Field of Search .......................... 549/264; 514/450

[56] References Cited

U.S. PATENT DOCUMENTS

| | | | |
|---|---|---|---|
| 4,469,682 | 9/1984 | Mrozik | 549/264 |
| 4,791,134 | 12/1988 | Barckhardt | 549/264 |

FOREIGN PATENT DOCUMENTS

| | | | |
|---|---|---|---|
| A/0142969 | 5/1985 | European Pat. Off. ............ | 549/264 |
| 84/10114 | 8/1985 | South Africa ...................... | 549/264 |

OTHER PUBLICATIONS

Chem Abst. 104, 109,603r, p. 724 (1986).

*Primary Examiner*—Richard L. Raymond
*Assistant Examiner*—Mark W. Russell
*Attorney, Agent, or Firm*—Edward McC. Roberts

[57] ABSTRACT the invention relates to novel C(29)-carbonyloxymilbemycin derivatives of formula I, to the preparation thereof and to the use thereof ffor controlling pests, as well as to pesticidal compositions which contain as active ingredient at least one of these compounds., Said novel compounds are of the general formula I

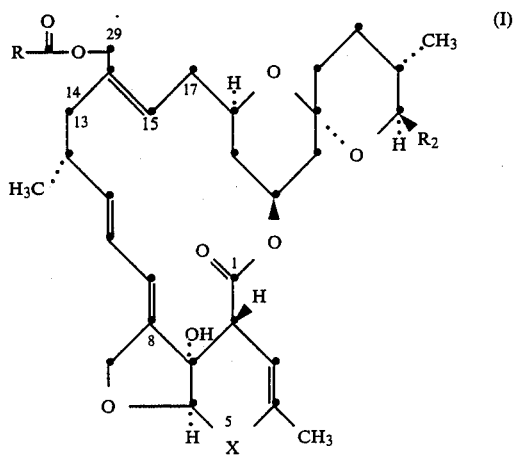

wherein
X is —CH(OR$_1$)—, —C(O)— or —C(=N—OH)—,
R$_1$ is hydrogen, a silyl group, an acyl group or a sugar residue,
R$_2$ is methyl, ethyl, isopropyl or sec-butyl and
R is hydrogen unsubstituted or substituted straight chain or branched C$_1$–C$_{18}$alkyl, unsubstituted or substituted C$_3$–C$_{10}$cycloalkyl, unsubstituted or substituted C$_2$–C$_6$alkenyl, unsubstituted or substituted C$_2$–C$_6$alkynyl or unsubstituted or substituted phenyl.

5 Claims, No Drawings

C(29)-CARBONYLOXYMILBEMYCIN DERIVATIVES FOR CONTROLLING PARASITIC PETS OF ANIMALS AND PLANTS

This is a continuation of application Ser. No. 022,198 filed on Mar. 5, 1987, now abandoned.

The present invention relates to novel C(29)-carbonyloxymilbemycin derivatives of formula I, to the preparation thereof and to the use thereof for controlling pests, as well as to pesticidal compositions which contain as active ingredient at least one of these compounds. Furthermore, important intermediates of formulae II and X are described.

The novel compounds are of the general formula I

[Structural formula I showing milbemycin derivative with labeled positions 5, 8, 13, 14, 15, 17, 29, and substituents R, R₂, X, OH, CH₃, H₃C]

wherein

X is —CH(OR$_1$)—, —C(O)— or —C(=N—OH)—,

R$_1$ is hydrogen, a silyl group, an acyl group or a sugar residue,

R$_2$ is methyl, ethyl, isopropyl or sec-butyl and

R is hydrogen, unsubstituted or substituted straight chain or branched $C_1$–$C_{18}$alkyl, unsubstituted or substituted $C_3$–$C_{10}$cycloalkyl, unsubstituted or substituted $C_2$–$C_6$alkenyl, unsubstituted or substituted $C_2$–$C_6$alkynyl or unsubstituted or substituted phenyl.

Within the scope of formula I, preferred representatives are those wherein X is —CH(OR$_1$)— or —C(O)—.

In the above definition, preferred meanings of R are $C_1$–$C_8$alkyl, $C_3$–$C_6$cycloalkyl, phenyl, halophenyl, $C_2$–$C_6$alkenyl and $C_2$–$C_6$alkynyl.

Possible substituents of the alkyl, cycloalkyl, alkenyl and alkynyl groups are for example 1 to 7 halogen atoms or 1 to 6 $C_1$–$C_6$alkoxy groups and possible substituents of the phenyl groups are 1 to 3 substituents selected from the group consisting of halogen atoms, $C_1$–$C_6$alkyl, $C_1$–$C_6$alkoxy, $C_1$–$C_4$alkylthio and nitro. These substituents, independently of one another, may be present in any arrangement. A further possible substituent of the alkyl group is an unsubstituted or substituted phenoxy group, e.g. a halogenated phenoxy group, preferably a phenoxy group which is substituted by 1 to 3 halogen atoms. The cycloalkyl groups may also be substituted by $C_1$–$C_4$alkyl groups.

Depending on the number of carbon atoms indicated, alkyl by itself or as moiety of another substituent will be understood as meaning for example the following groups: methyl, ethyl, propyl, butyl, pentyl, hexyl, heptyl, octyl, nonyl, decyl etc., as well as the isomers thereof, e.g. isopropyl, isobutyl, tert-butyl, isopentyl etc. Haloalkyl is a mono- to perhalogenated alkyl substituent, e.g. $CHCl_2$, $CHF_2$, $CH_2Cl$j $CCl_3$, $CF_3$, $CH_2F$, $CH_2CH_2Cl$, $CHBr_2$ etc. Throughout this specification, halogen will be understood as meaning fluorine, chlorine, bromine or iodine, with fluorine, chlorine or bromine being preferred. Alkenyl is an aliphatic hydrocarbon radical characterised by at least one C=C double bond, e.g. vinyl, 1-propenyl, allyl, 1-butenyl, 2-butenyl, 3-butenyl etc. Haloalkenyl is therefore such an alkenyl radical which is substituted by one or more halogen atoms. Alkynyl is a straight or branched carbon chain which is characterised by at least one C≡C triple bond. Typical representatives are for example ethynyl, 1-propionyl, propargyl, 1-butynyl etc. Alkoxyalkyl is an unbranched or branched alkyl group which is interrupted by an oxygen atom, e.g. $CH_2OCH_3$, $CH_2CH_2OCH_3$, $CH_2CH(CH_3)OCH_3$, $CH_2OC_2H_5$, $CH_2OC_3H_7$—i, $CH_2CH_2CH_2$—$OCH_3$ etc. Alkoxyalkoxyalkyl is an unbranched or branched alkyl group which is interrupted at each of two sites by an oxygen atom. Typical examples are: $CH_2OCH_2OCH_3$, $CH_2CH_2OCH_2OCH_3$, $CH_2OCH_2CH_2OCH_3$, $CH_2OCH_2OC_2H_5$, $CH(CH_3)OCH_2OC_3H_7$—i etc.

On account of their excellent activity against ectoparasites on productive livestock, the 5-oximes [X=—C(=N—OH)—] form an important subgroup within the scope of formula I.

Without any restrictions being implied, R is for example hydrogen, methyl, ethyl, propyl, isopropyl, n-butyl, sec-butyl, tert-butyl, neopentyl, chloromethyl, trifluoromethyl, trichloromethyl, trichlorethyl, trichloro-tert-butyl, 1,2,2,2-tetrachloroethyl, 1,3,3,3-tetrachloropropyl, 3-chloropropyl, ethenyl, propenyl, propynyl, methoxymethyl, isopropoxymethyl, 1-methyl-1-methoxyethyl, 2,2-dimethylvinyl, 1,2,2-trichlorovinyl, 1,3,3,3-tetrachloropropyl, 1,1-dichloro-2,2,2-trifluoroethyl, 1,3-pentadienyl, ethynyl, 1-propynyl, 1-butynyl, cyclopropyl, 2,2-dimethylcyclopropyl, 1-methylcyclopropyl, 2,2-dimethyl-3-(2,2-dichlorovinyl)cyclopropyl, cyclobutyl, cyclopentyl, cyclohexyl, phenyl, benzyl, p-tolyl, p-chlorophenyl, 2,6-dichlorophenyl or 2,4-dinitrophenyl, adamantyl or 4-fluorophenoxymethyl.

Within the scope of the present invention, a sugar residue shall be understood as meaning mono-, di- and trisaccharides, the hydroxy groups of which may be in etherified or esterified form. Typical representatives are e.g.:

monosaccharides: glucose, fructose, altrose, mannose, sorbose, gulose, idose, allose, galactose, ribose, arabinose, xylose, lyxose, erythrose, threose, thamnose and talose, as well as the corresponding derivatives thereof, such as methyl glucose, trimethyl glucose and tetraacetyl glucose, and also mono- or polyacetylated sugars;

disaccharides: lactose, maltose, cellobiose, melibiose and gentiobiose, as well as the corresponding derivatives thereof.

The carbohydrates indicated for formula I also comprise saccharides which additionally contain an amino radical, a thiol radical or a cyclic acetal radical formed from two adjacent OH groups and an aldehyde or ketone.

The saccharide bonded in the 5-position of the compounds of formula I may be in the form of an α-anomer or β-anomer. The present invention relates to both types of bonding.

Suitable substituents for the etherified or esterified form of the hydroxy groups of the sugar residues are, primarily, methyl, benzyl, an unsubstituted or halogenated $C_1$-$C_6$aliphatic acyl group, a benzoyl group or a $C_1$-$C_6$alkoxycarbonyl group.

Particularly preferred sugar residues are those of the formula

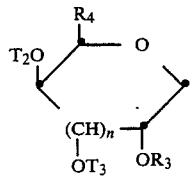

including the position isomers thereof, in which formula n is 0 or 1, $R_4$ is hydrogen, methyl or —$CH_2$—O—$T_1$, and each of $R_3$, $T_1$, $T_2$ and $T_3$ independently is hydrogen, methyl, benzyl, an unsubstituted or halogenated $C_1$-$C_6$aliphatic acyl group, a benzoyl group, or a $C_1$-$C_6$alkoxycarbonyl group, or $T_1$ and $T_2$ together with the carbon atom of the carbonyl group of an aliphatic or aromatic aldehyde or ketone form a cyclic acetal containing not more than 13 carbon atoms. Within the scope of formula I, said sugars form an interesting group of milbemycins.

The following are suitable for the formation of a cyclic acetal bonded to a sugar molecule: simple aldehydes such as acetaldehyde, propionaldehyde, butyraldehyde or benzaldehyde, or ketones such as acetophenone, cyclopentanone, cyclohexanone, cycloheptanone, fluorenone, methyl ethyl ketone and, in particular, acetone with the formation of corresponding acetonides.

Compounds of formula I wherein X is —CH(OR$_1$)— and R$_1$ is hydrogen are preferred. Acyl and silyl groups R$_1$ will in general be understood as being protective groups which, as is the case with the sugar residues, have no adverse effect on the biological activity of the substance.

Throughout this specification, compounds wherein R$_2$ is sec-butyl shall likewise be regarded as belonging to the class of milbemycin derivatives although according to conventional classification they are derived from avermectin derivatives. However, avermectin aglycones (carrying an OH group in the 13α-position) can be converted into milbemycin homologues in accordance with U.S. Pat. No. 4,173,571.

In naturally occurring milbemycins ($R_1$=H; $R_2$=$CH_3$, $C_2H_5$ or iso-$C_3H_7$), the substituent in the 13-position is always hydrogen. However, in avermectins an α-L-oleandrosyl-α-L-oleandrose radical which is attached through oxygen in the α-configuration to the macrolide molecule is in the 13-position. Moreover, avermectins differ structurally from milbemycins by the presence of a 23-OH group or $\Delta^{22,23}$ double bond and, usually, by the presence of a substituent $R_2$=sec—$C_4H_9$. By hydrolysing the sugar residue of avermectins, the corresponding avermectinaglycones containing an allylic 13α-hydroxy group are readily obtained. As stated above, avermectinaglycones can be converted into milbemycin homologues. In the milbemycin derivatives of the present invention, the $\Delta^{22,23}$ double bond always occurs in hydrogenated form.

On account of their pronounced parasiticidal and insecticidal activity, the following subgroups of compounds of formula I are particularly preferred:

Group Ia: Compounds of formula I, wherein X is —CH(OR$_1$)—, R$_1$ is hydrogen, R$_2$ is methyl, ethyl, isopropyl or sec-butyl and R has the following meanings:

$C_1$-$C_6$alkyl, $C_2$-$C_4$alkenyl, $C_2$-$C_4$alkynyl or $C_3$-$C_6$cycloalkyl, each unsubstituted or substituted by 1 to 4 halogen atoms or $C_1$-$C_4$-alkoxy;

phenyl which is unsubstituted or substituted by 1 to 3 substituents selected from the group consisting of halogen, $C_1$-$C_4$alkyl, $C_1$-$C_4$alkoxy, $C_1$-$C_4$alkylthio and nitro.

Group Ib: Compounds of formula I, wherein X is —CH(OR$_1$)—, R$_1$ is hydrogen, R$_2$ is methyl, ethyl, isopropyl or sec-butyl and R has the following meanings:

$C_1$-$C_5$alkyl, $C_2$-$C_3$alkenyl, $C_2$-$C_3$alkynyl or $C_3$-$C_6$cycloalkyl, each unsubstituted or substituted by 1 to 4 chlorine or fluorine atoms or methoxy;

phenyl which is unsubstituted or substituted by chlorine, fluorine, $C_1$-$C_2$alkyl, $C_1$-$C_2$alkoxy, $C_1$-$C_2$alkylthio or nitro.

Group Ic: Compounds of formula I, wherein X is —CH(OR$_1$)—, R$_1$ is hydrogen, R$_2$ is methyl or ethyl and R has the following meanings:

$C_1$-$C_5$alkyl, $C_2$-$C_3$alkenyl, $C_2$-$C_3$alkynyl or $C_3$-$C_6$cycloalkyl, each unsubstituted or substituted by 1 to 4 chlorine or fluorine atoms or methoxy;

phenyl which is unsubstituted or substituted by chlorine, fluorine, $C_1$-$C_2$alkyl, $C_1$-$C_2$alkoxy, $C_1$-$C_2$alkylthio or nitro.

Group Id: Compounds of formula I, wherein X is —CH(OR$_1$)—, R$_1$ is hydrogen, R$_2$ is isopropyl or sec-butyl and R has the following meanings:

$C_1$-$C_5$alkyl, $C_2$-$C_3$alkenyl, $C_2$-$C_3$alkynyl or $C_3$-$C_6$cycloalkyl, each unsubstituted or substituted by 1 to 4 chlorine or fluorine atoms or methoxy;

phenyl which is unsubstituted or substituted by chlorine, fluorine, $C_1$-$C_2$alkyl, $C_1$-$C_2$alkoxy, $C_1$-$C_2$alkylthio or nitro.

Group Ie: Compounds of formula I, wherein X is —CH(OR$_1$)—, R$_1$ is hydrogen, R$_2$ is methyl, ethyl, isopropyl or sec-butyl and R has the following meanings:

$C_1$-$C_5$alkyl, $C_2$-$C_3$alkenyl, $C_2$-$C_3$alkynyl or $C_3$-$C_6$cycloalkyl, each unsubstituted or substituted by 1 to 3 chlorine or fluorine atoms or methoxy;

phenyl which is unsubstituted or substituted by chlorine, fluorine, $C_1$-$C_2$alkyl, $C_1$-$C_2$alkoxy, $C_1$-$C_2$alkylthio or nitro.

Group If: Compounds of formula I, wherein X is —CH(OR$_1$)—, R$_1$ is hydrogen, R$_2$ is methyl or ethyl and R has the following meansings:

$C_1$-$C_5$alkyl, $C_2$-$C_3$alkenyl, $C_2$-$C_3$alkynyl or $C_3$-$C_6$cycloalkyl, each unsubstituted or substituted by 1 to 3 chlorine or fluorine atoms or methoxy.

Group Ig: Compounds of formula I, wherein X is —CH(OR$_1$)—, R$_1$ is hydrogen, R$_2$ is isopropyl or sec-butyl and R has the following meanings:

$C_1$-$C_5$alkyl, $C_2$-$C_3$alkenyl, $C_2$-$C_3$alkynyl or $C_3$-$C_6$cycloalkyl, each unsubstituted or substituted by 1 to 3 chlorine or fluorine atoms or methoxy.

Group Ih: Compounds of formula I, wherein X is —C(=N—OH)—, R$_2$ is methyl or ethyl and R has the following meanings:

$C_1$–$C_5$alkyl, $C_2$–$C_3$alkenyl, $C_2$–$C_3$alkynyl or $C_3$–$C_6$cycloalkyl, each unsubstituted or substituted by 1 to 3 chlorine or fluorine atoms or methoxy;

phenyl which is unsubstituted or substituted by chlorine, fluorine $C_1$–$C_2$alkyl, $C_1$–$C_2$alkoxy, $C_1$–$C_2$alkylthio or nitro.

Examples of particularly preferred 5-hydroxy derivatives of formula I are:

29-tert-butylcarbonyloxymilbemycin D, 29-cyclopropylcarbonyloxymilbemycin $A_4$, 29-tert-butylcarbonyloxymilbemycin $A_4$, 29-isobutylcarbonyloxymilbemycin $A_4$, 29-(2,2-dimethylpropyl)carbonyloxymilbemycin $A_4$ and 29-acetoxymilbemycin D.

Examples of preferred compounds of formula I carrying a protective group at the 5-hydroxy group are:

5-O-tert-butyldimethylsilyl-29-tert-butylcarbonyloxymilbemycin D,

5-O-tert-butyldimethylsilyl-29-cyclopropylcarbonyloxymilbemycin $A_4$,

5-O-tert-butyldimethylsilyl-29-acetoxymilbemycin D,

5-O-tert-butyldimethylsilyl-29-tert-butylcarbonyloxymilbemycin $A_4$,

5-O-tert-butyldimethylsilyl-29-(2,2-dimethylcarbonyloxymilbemycin $A_4$,

5-O-tert-butyldimethylsilyl-29-isobutylcarbonyloxymilbemycin $A_4$ and

5-O-2′,3′,4′6′-tetra-O-acetylgalactose-29-tert-butylcarbonyloxymilbemycin D.

In accordance with the present invention, the compounds of formula I are prepared by reacting either a compound of formula II

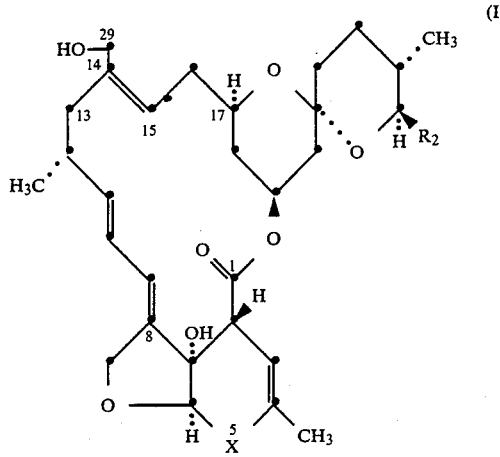

or a compound of formula III

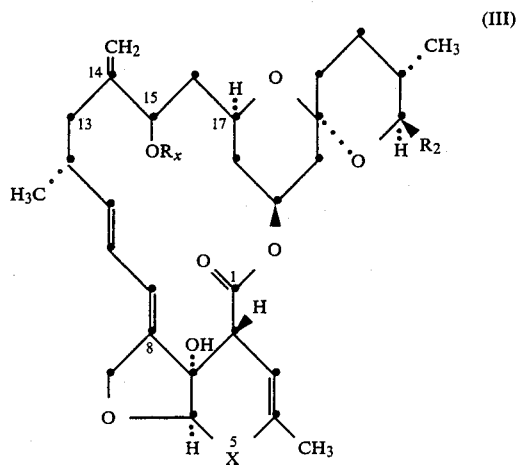

in which formulae II and III $R_2$ is as defined for formula I, X is —CH(OR$_1$)—, $R_1$ being an OH protective group, or X is —C(O)—, and $R_x$ in formula III is hydrogen or a readily removable group, with an acid of formula IV

R—COOH    (IV)

wherein R is as defined for formula I, or with a derivative of said acid, which derivative is capable of introducing an ester group, or first converting the compound of formula III into a compound of formula II by saponification of the OR$_x$ group and then reacting the resultant compound of formula II with an acid of formula IV, and, if desired, converting the resultant compound of formula I into a 5-hydroxy derivative of formula I by removing the OH protective group, and, if desired, converting said 5-hydroxy derivative into a silyl derivative by subsequent silylation or into a sugar derivative of formula I by introducing a sugar residue, and, if a compound of formula I wherein X is —C(=N—OH)— is desired, reacting a 5-ketone of formula I with hydroxylamine or with a salt thereof.

On account of their specific structure, the compounds of formulae II and III are predestined for the preparation of the valuable final products of formula I and constitute an object of the present invention.

Examples of acid derivatives of the acid of formula IV which are capable of introducing an ester group are:

(a) its acid amides of formula V

RCON(Alkyl)$_2$    (V)

wherein the alkyl moieties contain 1 to 4 carbon atoms and are preferably methyl, (b) its acid halides of formula VI RCOhal    (VI)

wherein hal is halogen, preferably chlorine or bromine, and (c) its acid anhydride of formula VII (RCO)$_2$O    (VII).

R in the above formulae V to VII is as defined for formula I.

The reactions for the preparation of compounds of formula I are conveniently carried out with compounds of formula II or III in which the reactive 5-hydroxy group is protected.

Throughout this specification, OH protective groups $R_1$ shall in general understood as being those protective functions customarily encountered in organic chemistry. Such protective groups are, in particular, acyl and silyl groups. Examples of suitable acyl groups are the radicals $R_5$—C(O)—, wherein $R_5$ is $C_1$–$C_{10}$alkyl, $C_1$–$C_{10}$haloalkyl, or a phenyl or benzyl radical which is unsubstituted or substituted by substituents selected from the group consisting of halogen, $C_1$–$C_3$alkyl, $C_1$–$C_3$haloalkyl, $C_1$–$C_3$alkoxy, $C_1$–$C_3$haloalkoxy, cyano and nitro, with the preferred meanings of $R_5$ being $C_1$–$C_6$alkyl, $C_1$–$C_6$haloalkyl, or phenyl which is unsubstituted or substituted by halogen, $C_1$–$C_3$alkyl, $CF_3$ or nitro. Suitable silyl groups $R_1$ are the radicals —Si($R_6$)($R_7$)($R_8$), wherein $R_6$, $R_7$ and $R_8$, preferably independently of one another, are $C_1$–$C_4$alkyl, benzyl or phenyl and form for example one of the groups trimethylsilyl, diphenyl-tert-butylsilyl, bis(isopropyl)methylsilyl, triphenylsilyl etc. or, preferably, tert-butyldimethylsilyl. The 5-OH group may also be in the form of benzyl ether or methoxyethoxymethyl ether.

Compounds of formula I wherein $R_1$ is a protective group can be converted by simple, e.g. hydrolytic, removal of the protective function into the highly active free 5-hydroxy derivatives ($R_1$=H) and therefore act as intermediates. However, the biological value of these compounds is not diminished by the protective group or the sugar residue.

The process is generally carried out in an inert solvent or in one of the reactants provided these are liquid. Examples of suitable solvents are: ethers and ethereal compounds such as dialkyl ethers (diethyl ether, diisopropyl ether, tert-butylmethyl ether, dimethoxyethane, dioxane, tetrahydrofuran, anisole and the like); halogenated hydrocarbons such as chlorobenzene, methylene chloride, ethylene chloride, chloroform, carbon tetrachloride, tetrachloroethylene and the like; or sulfoxides such as dimethyl sulfoxide; as well as aromatic or aliphatic hydrocarbons such as benzene, toluene, xylenes, petroleum ether, ligroin, cyclohexane and the like. In some cases it may be of advantage if the reactions are carried out in an inert gas atmosphere (e.g. argon, helium, nitrogen and the like) and/or in absolute solvents. If desired, the final products may be purified in conventional manner, e.g. by washing, digesting, extraction, recrystallisation, chromatography etc.

The reaction of compounds of formula II with acid halides of formula VI or acid anhydrides of formula VII is normally carried out in the above inert solvents in general in the temperature range from 0° to 100° C., preferably from 20° to 60° C. In order to neutralise the acids which form as by-products during the reaction, it is convenient to carry out the reaction in the presence of a neutralising agent. A catalyst such as p-dimethylaminopyridine may also be added.

Suitable neutralising agents are organic bases, e.g. tertiary amines such as trialkylamines (trimethylamine, triethylamine, diisopropylmethylamine, tripropylamine and the like), pyridine and pyridine bases (4-dimethylaminopyridine, 4-pyrrolidylaminopyridine and the like), with pyridine being preferred. The neutralising agent is usually employed in at least equimolar amount, based on the starting materials. The organic bases may also be employed as solvents.

If the acid of formula IV is employed as reagent, then the reaction is conveniently carried out in the presence of dehydrating agents. The reaction is carried out for example in the presence of dicyclohexylcarbodiimide and pryidine or in the presence of dialkyl azodicarboxylate and triphenylphosphine.

The reaction of compounds of formula II with acid amides of formula V is preferably carried out in the presence of orthoesters and in the presence of catalytic amounts of an acid. Acids suitable for the catalysis of the reaction are protonic acids or Lewis acids. Examples of such acids are inorganic acids, e.g. hydrohalic acids such as hydrochloric acid, hydrobromic acid or hydriodic acid, perchloric acid and sulfuric acid, and organic acids such as acetic acid, trifluoroacetic acid, trichloroacetic acid, propionic acid, oxalic acid, formic acid, benzenesulfonic acid, p-toluenesulfonic acid, methanesulfonic acid and the like, as well as Lewis acids such as $BF_3$, $AlCl_3$, $ZnCl_2$ and the like. Particularly preferred acids are p-toluenesulfonic acid and sulfuric acid.

The orthoesters required for this reaction are of formula VIII $$R_yC(OR_z)_3 \qquad (VIII)$$

wherein $R_y$ is hydrogen or $C_1$–$C_4$alkyl, preferably methyl, and $R_z$ is $C_1$–$C_4$alkyl, preferably methyl or ethyl.

When using acid amides of formula V for the preparation of compounds of formula I, the reaction temperatures are generally in the range from 0° to 150° C., preferably from 20° to 130° C.

The reaction of 15-derivatives of formula III with an acid of formula IV or with a reactive derivative thereof is normally carried out in the presence of one of the above-mentioned inert solvents. Said reaction can be performed either in the presence of one of the above-mentioned bases or, alternatively, in the presence of an acid. Suitable acids are, in particular, sulfonic acids, e.g. p-toluenesulfonic acid, methanesulfonic acid or camphorsulfonic acid. In general, the addition of an acid of formula IV to the compound of formula III is effected in the temperature range from 0° to 100° C., preferably from 30° to 60° C.

The 29-substituted milbemycins of formula II are obtained by an allylic substitution (SN2'). The 29-hydroxymilbemycins are obtained in the absence of an acid of formula IV, but in the presence of water. Said latter allylic substitution is normally carried out in the temperature range from 0° to 80° C., preferably from 20° to 50° C.

Within the scope of the present invention, examples of readily removable groups $R_x$ in formula III are, in particular, acyl groups such as formyl, acetyl, benzoyl, ethoxycarbonyl or P(=O)(O alkyl)$_2$, e.g. P(O)(OEt)$_2$, and also alkylsulfonyl radicals such as benzenesulfonyl, paratosyl or, preferably, lower alkylsulfonyl, most preferably mesyl, and, in certain cases, tetrahydropyranyl.

The preparation of compounds of formula I which carry a sugar residue bonded to the oxygen atom in the 5-position is a derivativisation of the reactive 5-hydroxy group ($R_1$=H) with a suitable sugar molecule and is carried out in accordance with a bonding method employed in sugar chemistry, e.g. in accordance with Koenigs-Knorr synthesis, the silver triflate process, the orthoester method, phenylthio synthesis or 2-pyridylthio synthesis.

(A) In accordance with Koenigs-Knorr synthesis or the silver triflate process, a 5-hydroxymilbemycin of formula I ($R_1=H$) can be bonded, in the presence of a silver salt or mercury salt as condensing agent, with the sugar residue to be introduced, wherein all OH groups are protected, with the exception of the chlorine- or bromine-substituted 1-OH group, in the temperature range from $-30°$ C. to $+60°$ C., preferably from $-5°$ C., to $+30°$ C., with the exclusion of light.

Suitable silver salts are freshly precipitated Ag$_2$O or, preferably, Ag$_2$CO$_3$ or CF$_3$—COOAg. A particularly preferred silver salt is silver trifluoromethanesulfonate (silver triflate=CF$_3$—SO$_3$Ag), in the presence of which the glycosidation takes place quickly even at temperatures below 0° C. In order to activate the 5-OH group of the 5-hydroxymilbemycin and to neutralise any CF$_3$—CO$_3$H or CF$_3$—COOH forming, it is convenient to add a tertiary amine (e.g. triethylamine, diisopropylethylamine, diazabicycloundecane and the like) to the reaction solution.

If desired, the protective groups can subsequently be removed by mild saponification (e.g. NH$_3$/CH$_3$OH). Suitable solvents for this partial step are in particular anhydrous aprotic solvents such as dichloromethane, acetonitrile, benzene, toluene, nitromethane, dioxane, tetrahydrofuran, ethylene glycol dimethyl ether; diethyl ether is particularly suitable.

The protected 1-chloro- or 1-bromo-sugar is employed in equimolar amount, based on the 5-hydroxymilbemycin of formula I. However, it is preferably employed in excess, i.e. 1.5 to 3 times the equimolar amount. In order to obtain a satisfactory yield, the duration of the reaction is from 5 to 72 hours.

In place of the silver salt, mercuric cyanide or a combination of mercuric oxide with either mercuric chloride or mercuric bromide may also be employed (Helferich synthesis).

In accordance with a further variant, the reactivity in the 1'-position of the sugar to be bonded glycosidically, the further OH groups of which must be protected, can be increased by initially converting said sugar into the 1'-phenylthio derivative and subsequently reacting this derivative with DAST (=diethylaminosulfur trifluoride) in absolutely dry dichloromethane (molar sieve) at a temperature in the range from $+5°$ C. to $-30°$ C. to give the 1'-fluorine derivative. Compared with the corresponding 1'-chlorine or 1'-bromine derivative employed in Koenigs-Knorr synthesis, said 1'-fluorine derivative of the sugar reactant can be bonded more reactively with a 5-hydroxymilbemycin of formula I, in the presence of SnCl$_2$ and AgClO$_4$, in a dry aprotic solvent such as diethyl ether, in an inert gas atmosphere (e.g. argon) and at a temperature in the range from $+5°$ C. to $-30°$ C. (q.v. J. Am. Soc. 1984, 106, pp. 4189–4192).

(B) A better reaction is obtained if the likewise protected carbohydrate to be activated in the 1'-position is converted, at about 0° C. and in an argon atmosphere, with 2,2-dithiopyridine in dry dichloromethane into the 1'-S-(2-pyridyl)carbohydrate which readily reacts with the free 5-OH group of the 5-hydroxymilbemycin, in the presence of Pb(ClO$_4$)$_2$ or AgClO$_4$ as condensing agent, at room temperature and in tetrahydrofuran as solvent, to form the glycosidic bond (q.v. J. Org. Chem. 1983, 48, pp. 3489-3493).

(C) Glycosidic bonds can also be formed in the presence of Lewis acids such as AlCl$_3$, AlBr$_3$, SnCl$_4$, ZnCl$_2$, BF$_3$ (and, in particular, the etherate thereof), with acetylated sugars being particularly suitable for this type of bonding (q.v. Chimia 21, 1967, pp. 537–538).

(D) In accordance with the orthoester method, glycosidic bonds can also be formed by reacting the milbemycin with the sugar to be bonded, the OH groups of which sugar are protected, in the presence of the orthoester of a lower alcohol, one alcoholic component of which is the sugar reactant.

The process for the preparation of 5-sugar-milbemycin derivatives, of formula I comprises, in the narrower sense, reacting a 5-hydroxymilbemycin of formula I (a) with the sugar residue to be introduced, wherein all OH groups are protected, with the exception of the anomeric 1-OH group substituted in the 1-position by chlorine or bromine, in the presence of a silver salt or mercury salt as condensing agent, with the exclusion of light and in the temperature range from $-30°$ C. to $+60°$ C., preferably from $-5°$ C. to $+30°$ C.; or (b) with the sugar residue to be introduced, wherein all OH groups are protected, with the exception of the anomeric 1-OH group substituted in the 1-position by fluorine, in the presence of SnCl$_2$ and AgClO$_4$ as condensing agents, with the exclusion of light and in the temperature range from $+5°$ C. to $-30°$ C.;

and, if desired, mildly saponifying the hydroxy protective groups.

The oximes [X=—C(=N—OH)—] of formula I are prepared by reacting a 5-keto compound [X=—C-(O)—] of formula I with hydroxylamine or a salt thereof, preferably a mineral salt thereof, most preferably the hydrochloride thereof. The reaction is conveniently carried out in a suitable solvent, e.g. a lower alkanol such as methanol, ethanol or propanol; an ethereal compound such as tetrahydrofuran or dioxane; an aliphatic carboxylic acid such as acetic acid or propionic acid; water or in mixtures of these solvents with one another or with other customary inert solvents. The reaction temperatures may vary within wide ranges. It is convenient to carry out the reaction in the range from about $+10°$ to $+100°$ C. If hydroxylamine is employed in the form of one of its salts, e.g. in the form of its hydrochloride, then in order to neutralise the acid (e.g. HCl) it is advantageous to add a base customarily employed for such purposes and to perform the reaction in the presence of a hydrophilic agent, e.g. a molecular sieve. Suitable bases are both organic and inorganic bases, e.g. tertiary amines such as trialkylamines (trimethylamine, triethylamine, tripropylamine and the like), pyridine and pyridine bases (4-dimethylaminopyridine, 4-pyrrolidylaminopyridine and the like), oxides, hydrides and hydroxides, carbonates and bicarbonates of alkali metals and alkaline earth metals (CaO, BaO, NaOH, KOH, NaH, Ca(OH)$_2$, KHCO$_3$, NaHCO$_3$, Ca(HCO$_3$)$_2$, K$_2$CO$_3$, Na$_2$CO$_3$), as well as alkali metal acetates such as CH$_3$COONa or CH$_3$COOK. Alkali metal alcoholates such as C$_2$H$_5$ONa and C$_3$H$_7$—nONa are also suitable bases. Triethylamine is preferred.

In accordance with the present invention, the compounds of formula II are obtained by an oxidative allylic rearrangement from 15-hydroxymilbemycin derivatives of formula IX

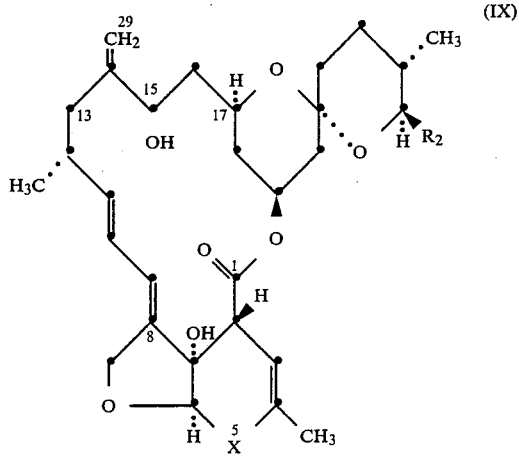

(IX)

wherein X and R$_2$ are as defined for formula I, and subsequent selective reduction of the 29-aldehyde obtained as intermediate.

The reaction can be illustrated as follows:

First partial step: Oxidative allylic rearrangement

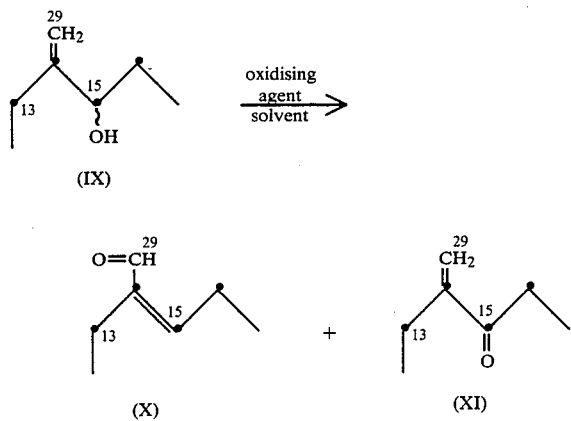

of the allyl alcohol of formula IX to give a 29-oxo compound of formula X. In said reaction, the allyl alcohol of formula IX is rearranged by oxidation with a suitable oxidising agent in an inert solvent to give the corresponding aldehyde (=29-oxo compound) of formula X. In general, the corresponding unsaturated ketone of formula XI is formed as by-product in the course of the reaction. This by-product is itself an intermediate since, on account of its reactivity, it can be employed for the synthesis of further milbemycin derivatives. Normally the trans- and cis-forms of the aldehyde of formula X are formed side by side, with the trans-form generally predominating.

The 29-oxo compounds of formula X have the following chemical structure

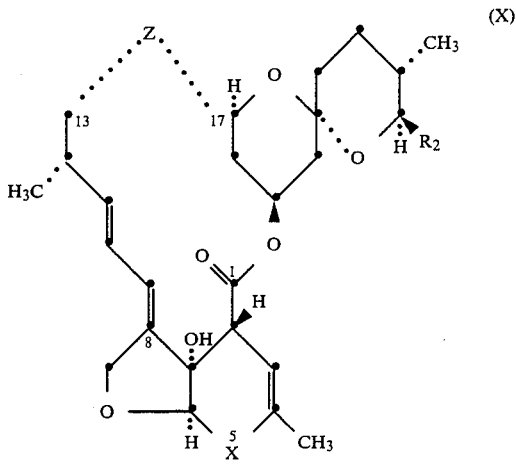

(X)

wherein Z is one of the groups

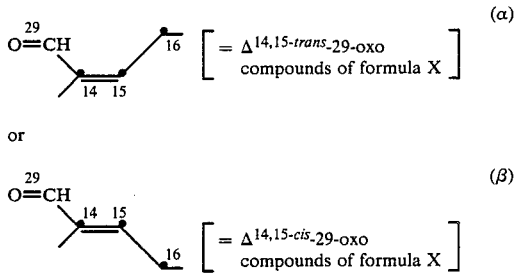

and X and R$_2$ are as defined for formula I. Owing to their specific structure, said compounds of formula X, as direct precursors for the preparation of compounds of formula II, are predestined for the preparation of the valuable final products of formula I. Accordingly, the compounds of formula X constitute a further object of the present invention.

Suitable reagents for the (oxidative) rearrangement are, in particular, chromium(VI) compounds, e.g. pyridinium chromate, pyridinium chlorochromate and the like. It is convenient to carry out the reaction in an inert solvent. Examples of suitable solvents are ethers and ethereal compounds such as dialkyl ethers (diethyl ether, diisopropyl ether, tert-butylmethyl ether, dimethoxyethane), dioxane, tetrahydrofuran, anisole and the like; halogenated hydrocarbons such as chlorobenzene, methylene chloride, ethylene chloride, chloroform, carbon tetrachloride, tetrachloroethylene and the like; sulfoxides such as dimethyl sulfoxide; amides such as N,N-dimethylformamide; esters such as ethyl acetate, propyl acetate, butyl acetate and the like; as well as mixtures of these solvents with one another or with water and/or other customary inert solvents such as benzene, xylene, petroleum ether, ligroin, cycohexane and the like. In some cases, it may prove advantageous to perform the reaction or partial steps thereof under an inert gas atmosphere (e.g. argon, helium, nitrogen and the like) and/or in absolute solvents. If desired, intermediates can be isolated from the reaction medium and, if required, purified in conventional manner before further reaction, e.g. by washing, dispersing, extraction, recrystallisation, chromatography etc. However, it is possible to dispense with such intermediary purification steps, i.e. by only purifying the corresponding final products. The reaction temperature for the oxidative allylic rearrangement is normally in the range from −50° to +50° C., preferably from −10° to +30° C. The reaction time depends essentially on the reaction temperatures and varies in general from 10 minutes to about 12 hours.

The ketones of formula XI

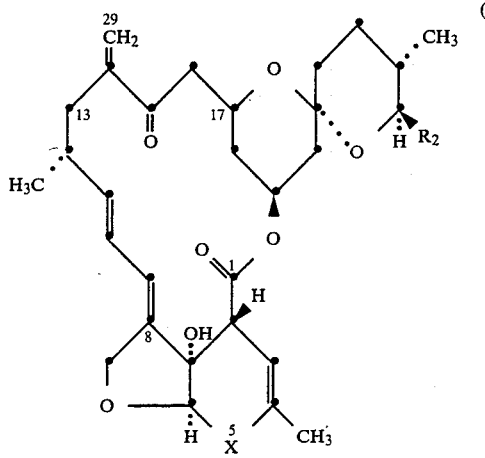

(XI)

wherein X and $R_2$ are as defined for formula I, constitute an object of the present invention. Owing to their structure, said ketones are suitable as intermediates for the preparation of further milbemycin derivatives and themselves also exhibit parasitic activity.

Second partial step: Reduction of the 29-oxo compound of formula X to the 29-hydroxy compound of formula II

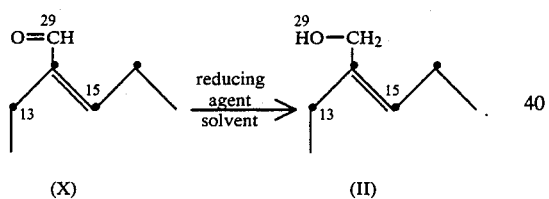

The aldehyde of formula X obtained in the first partial step (see above) is reduced in a suitable solvent to a 29-hydroxy compound of formula II.

Examples of suitable reducing agents are hydrides such as lithium aluminium hydride, sodium borohydride, sodium cyanoborohydride, lithium tri-sec-butyl borohydride, lithium triethyl borohydride, lithium tri-tert-butoxy aluminium hydride and compounds such as 9-borobicyclo[3.3.1]nonane and the like. Depending on the reducing agent, suitable solvents are e.g. alcohols, in particular alkanols such as methanol, ethanol, propanol, butanol and the like, and also water, carboxylic acids such as acetic acid, aromatic hydrocarbons such as benzene, toluene, xylenes and the like, or ethereal substances such as dialkyl ethers, e.g. diethyl ether, diisopropyl ether, tert-butylmethyl ether, dioxane, tetrahydrofuran and similar compounds. It may be of advantage to add a catalyst, e.g. a catalytic amount of a strong acid such as sulfuric acid, hydrochloric acid and the like, or of a cerium(III) salt. This reaction is carried out in the temperature range from −20° to +40° C., preferably from 0° to +30° C.

The reduction of the trans-form of a compound of formula X yields the trans-form of a compound of formula II and, accordingly, the reduction of the cis-form of a compound of formula X yields the cis-form of a compound of formula II.

If the aldehyde of formula X is in the trans-form and contains no protective group (silyl group) at the oxygen atom in the 5-position, then trans-cis-isomerism is observed at a temperature as low as room temperature.

The 29-oxo compounds obtained as intermediates, which compounds may also be isolated and which have the general formula X

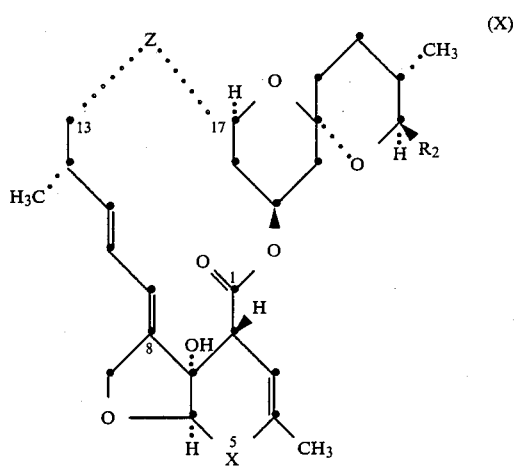

(X)

wherein Z is one of the groups

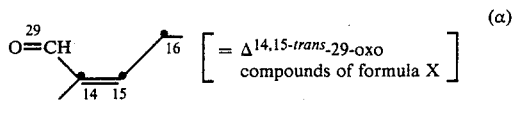

(α)

or

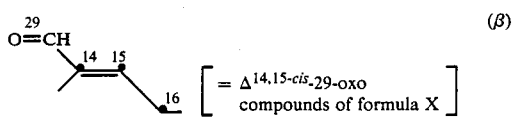

(β)

and X are $R_2$ are as defined for formula I, are predestined for the preparation of compounds of formula II not only on account of their specific structure but also owing to the fact that they themselves exhibit ectoparasitic, endoparasitic and, in some cases, insecticidal activity in the same area of indications as the final products of formula I.

Accordingly, the compounds of formula X likewise constitute an object of the present invention.

The starting compounds of formula IX can be obtained by singulett oxygen oxidation from appropriately substituted milbemycin derivatives of formula XII

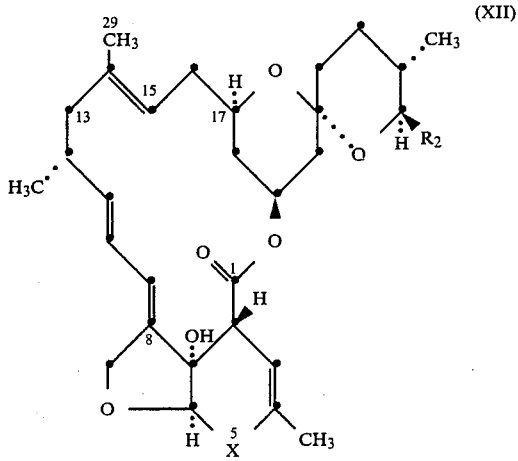

wherein X and R₂ are as defined for formula I, and subsequent selective reduction of the 15-peroxide obtained as intermediate

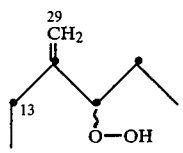

15-peroxide with sodium borohydride, lithium aluminium hydride or triphenylphosphine. The reaction is carried out in visible light in the presence of a sensitiser, under normal pressure and in the temperature range from −90° C. to +45° C., preferably from 0° to +20° C., in an inert solvent. It is preferred to carry out the reaction in an irradiating apparatus.

The reaction course can be illustrated as follows:

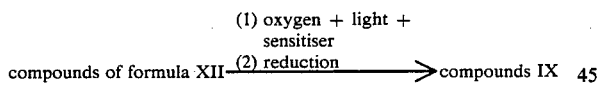

(q.v. H. H. Wassermann et al, "Singulett Oxygen", Academic Press, New York 1979; or B. Randy et al., "Singulett Oxygen Reactions with Organic Compounds and Polymers", Wiley, N.Y. 1978).

Examples of suitable solvents are ethers and ethereal compounds such as diethyl ether, diisopropyl ether, dioxane and tetrahydrofuran; aromatic hydrocarbons such as benzene, toluene and xylenes; ketones such as acetone, methyl ethyl ketone and cyclohexanone; nitriles such as acetonitrile; esters such as ethyl acetate and butyl acetate; and dimethylformamide, dimethyl sulfoxide and halogenated hydrocarbons; or mixtures of these solvents with water.

Suitable sensitisers are dyes such as methylene blue, Bengal pink, chlorophyll, erysathrosin, eosine, zinc tetraphenyl porphine, hematoporphyrin, riboflavine, fluorescein or acridine orange. Selective reduction is carried out in the temperature range from 0° to 20° C., without further working up, after conclusion of the oxidation.

As light source it is convenient to use a lamp having a strength of 60 to 500 watt, preferably of 100 to 350 watt. If it is desired to protect the 5-hydroxy group, then suitable protective groups are the silyl and acyl groups mentioned for R₁ or e.g. a benzyl ether, methoxyethoxymethyl ether, or dihydrofuran or dihydropyran radicals. These protective groups can be introduced into compounds of formula XII and later removed again in conventional manner.

The compounds of formula XII wherein R₁ is hydrogen have either become known from U.S. Pat. No. 3,950,360 and were originally designated as "Antibiotics B-41-A", later called "milbemycin A" compounds, or they are known from U.S. Pat. No. 4,346,171d and are designated as "B-41" or "milbemycin D" or they have become known from U.S. Pat. No. 4,173,571 and are designated as 13-deoxy-22,23-dihydroavermectins (R₂=sec-butyl). They possess the structure of formula XIII

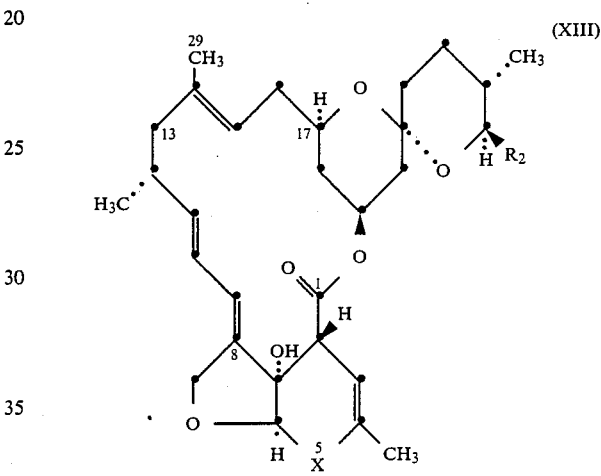

R₂=CH₃ milbemycin A₃
R₂=C₂H₅ milbemycin A₄
R₂=isoC₃H₇ milbemycin D
R₂=sec-C₄H₉ 13-deoxy-22,23-dihydro-C-076-Bla-aglycone or 13-deoxy-22,23-dihydroavermectin-Bla-aglycone.

The compounds of formula III can be obtained from the 15-hydroxymilbemycin of formula IX on which they are based

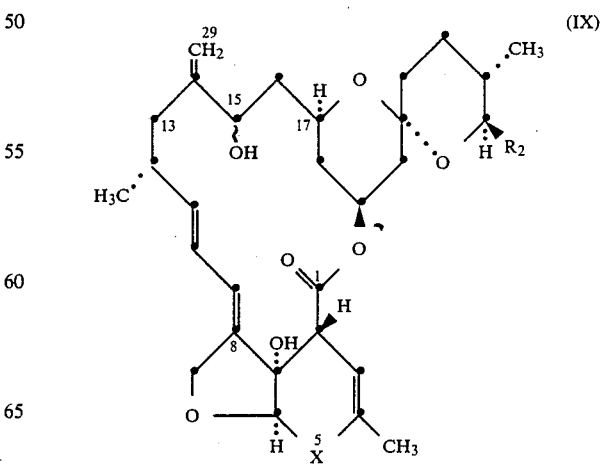

by introducing the removable group $R_x$, i.e. by esterifying a compound of formula IX by reaction with the acid radical, e.g. an acid anhydride or acid halide, preferably an acid chloride or bromide, in the presence of one of the above-mentioned bases in an inert solvent. This esterification reaction is usually carried out in the temperature range from $-30°$ C. to $+80°$ C., preferably from 0° to 50° C.

By acylating or silylating the 5-OH group, all those milbemycin derivatives are prepared wherein $R_1$ has a meaning other than hydrogen ($R_1$=OH protective group). For the silylation it is convenient to use a silane of the formula Y-Si($R_6$)($R_7$)($R_8$), wherein each of $R_6$, $R_7$ and $R_8$ is one of the radicals indicated above and Y is a silyl leaving group. Examples of silyl leaving groups Y are bromide, chloride, cyanide, azide, acetamide, trifluoroacetate or trifluoromethanesulfonate. This recitation constitutes no limitation; further typical silyl leaving groups are known to the skilled person.

5-O-silylations are carried out in anhydrous medium, preferably in inert solvents and, most preferably, in aprotic solvents. The reaction conveniently takes place in the temperature range from 0° to $+80°$ C., preferably from $+10°$ to $+40°$ C. It is preferred to add an organic base. Examples of suitable bases are tertiary amines such as triethylamine, triethylenediamine, triazole and, preferably, pyridine, imidazole or 1,8-diazabicyclo[5.4.0]-undec-7-ene (DBU).

The removal of these silyl radicals $R_1$ in the 5-position is effected by selective mild hydrolysis ($\rightarrow R_1 =$H) with e.g. arylsulfonic acid in alcoholic solution or in accordance with another method known to the skilled person.

The described process for the preparation of compounds of formula I constitutes in all its partial steps an object of the present invention.

The compounds of formula I are most suitable for controlling pests of animals and plants, including in particular ectoparasites of animals. These last mentioned pests comprise those of the order Acarina, in particular pests of the families Ixodidae, Dermanyssidae, Sarcoptidae, Psoroptidae; of the orders Mallophaga, Siphonaptera, Anoplura (e.g. family of the Haematopinidae); and of the order Diptera, in particular pests of the families Muscidae, Calliphoridae, Oestridae, Tabanidae, Hippoboscidae, and Gastrophilidae.

The compounds of formula I can also be used against hygiene pests, especially of the order Diptera (families Sarcophagidae, Anophilidae and Culicidae); of the order Orthoptera, of the order Dictyoptera (e.g. family of the Blattidae), and of the order Hymenoptera (e.g. family of the Formicidae).

The compounds of formula I also have a lasting action against mites and insects which are parasites of plants. When used to control spider mites of the order Acarina, they are effective against eggs, nymphs and adults of Tetranychidae (Tetranychus spp. and Panonychus spp.). They also have excellent activity against sucking insects of the order Homoptera, in particular against pests of the families Aphididae, Delphacidae, Cicadellidae, Psyllidae, Coccidae, Diaspididae and Eriophyididae (e.g. the rust mite on citrus fruit); of the orders Hemiptera, Heteroptera and Thysanoptera; and against plant-feeding insects of the orders Lepidoptera, Coleoptera, Diptera and Orthoptera.

The compounds of formula I are also suitable for use against soil pests.

The compounds of formula I are therefore effective against all development stages of sucking and feeding insects in crops such as cereals, cotton, rice, maize, soybeans, potatoes, vegetables, fruit, tobacco, hops, citrus fruit, avocados and others.

The compounds of formula I are also effective against plant nematodes of the species Meloidogyne, Heterodera, Pratylenchus, Ditylenchus, Radopholus, Rhizoglyphus and others.

Furthermore, the compounds of formula I act against helminths, among which the endoparasitic nematodes can be the cause of severe diseases in mammals and fowl, for example in sheep, pigs, goats, cattle, horses, donkeys, dogs, cats, guinea pigs, cage-birds. Typical nematodes having this indication are: Haemonchus, Trichostrongylus, Ostertagia, Nematodirus, Cooperia, Ascaris, Bunostomum, Oesphagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. The particular advantage of the compounds of formula I is their activity against those parasites which are resistant to benzimidazole-based parasiticides.

Certain species of the genera Nematodirus, Cooperia and Oesophagostomum attack the intestinal tract of the host animal, whereas others of the species Haemonchus and Ostertagia parasiticise in the stomach and those of the species Dictyocaulus in the lung tissue. Parasites of the families Filariidae and Setariidae are found in internal cell tissue and internal organs, e.g. in the heart, blood vessels, lymph vessels and in subcutaneous tissue. In this connection, particular mention is to be made of the dog heartworm, *Dirofilaria immitis*. The compounds of formula I are highly effective against these parasites.

The compounds of formula I are also suitable for controlling pathogenic parasites in humans, among which parasites there may be mentioned as typical representatives occurring in the alimentary tract those of the species Ancylostoma, Necator, Ascaris, Strongyloides, Trichinella, Capillaria, Trichuris and Enterobius. The compounds of this invention are also effective against parasites of the species Wuchereria, Brugia, Onchocerca and Loa of the family of the Filariidae which occur in the blood, in tissue and various organs, and, in addition, against Dracunculus and parasites of the species Strongyloides and Trichinella which infest in particular the gastro-intestinal tract.

The compounds of formula I are used in unmodified form or, preferably, together with the adjuvants conventionally employed in the art of formulation, and are therefore formulated in known manner e.g. to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The compounds of formula I are administered to warm-blooded animals at rates of application of 0.01 to 10 mg/kg of body weight. They are applied to enclosed crop areas in amounts of 10 g to 1000 g per hectare. They are also used in pens, livestock buildings or other buildings.

The formulations, i.e. the compositions, preparations or mixtures containing the compound of formula I (active ingredient) are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the active ingredient to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide or phospholipids.

The surfactants customarily employed in the art of formulation are described e.g. in "McCutcheon's Detergents and Emulsifiers Annual", MC Publishing Corp., Ridgewood, N.J., 1982.

The pesticidal compositions usually contain 0.01 to 95%, preferably 0.1 to 80%, of a compound of formula I, 5 to 99.99% of a solid or liquid adjuvant, and 0 to 25%, preferably 0.1 to 25%, of a surfactant.

Whereas commercial products are preferably formulated as concentrates, the end user will normally employ dilute formulations having a concentration of 1–10,000 ppm.

The invention therefore also relates to pesticidal compositions which contain as active ingredient at least one compound of formula I, together with customary carriers and/or dispersing agents.

The compositions may also contain further ingredients, such as stabilisers, antifoams, viscosity regulators, binders, tackifiers as well as fertilisers or other active ingredients for obtaining special effects.

PREPARATORY EXAMPLES

Preparation of Starting Materials and Intermediates

Example S1: Preparation of the compounds $\Delta^{14,29}$-15-hydroxymilbemycin D (formula IX) and 14-hydroxy-$\Delta^{15,16}$-milbemycin D from milbemycin D In a glass irradiation apparatus, a solution of 5.56 g of milbemycin D and 0.03 g of methylene blue in 400 ml of acetonitrile is irradiated, under a stream of oxygen, with visible light for 10 hours at a temperature of 20° C. (200 watt projector lamp). The reaction mixture is then reduced with 3.9 g of triphenylphosphine at 20° C. The reaction mixture is concentrated, and the residue is chromatographed through a column of silica gel eluted with a 3:1 mixture of methylene chloride and ethyl acetate, affording 4.10 g of $\Delta^{14,29}$-5-hydroxy-milbemycin D with a melting point of 228°–229° C.; mass spectrum m/e: 572 (M+), 554.

Also obtained is 0.34 g of 14-hydroxy-$\Delta^{15,16}$-milbemycin D with a melting point of 252°–254° C.; mass spectrum m/e: 572 (M+), 554.

Example S2: Preparation of the compounds 5-keto-$\Delta^{14,29}$-15-hydroxymilbemycin D (formula IX) and 5-keto-14-hydroxy-$\Delta^{15,16}$-milbemycin D from 5-keto-milbemycin D (a) Preparation of 5-keto-milbemycin D A mixture of 1 g of milbemycin D, 2 g of activated manganese dioxide and 50 ml of anhydrous methylene chloride is stirred for 4 hours at 20°–25° C. The reaction mixture is filtered, and the filtrate is purified through a short column (about 30 cm) of silica gel, affording 1 g of yellowish amorphous 5-keto-milbemycin with a melting point of 152°–157° C.

(b) The singulett oxidation of the 5-keto-milbemycin prepared in (a) and the further working up are effected by the method described in Example S1. After chromatography through silica gel there is obtained 0.6 g of 5-keto-$\Delta^{14,29}$-15-hydroxy-milbemycin D with a melting point of 160°–165° C.; mass spectrum m/e: 570 (M+), 552. Also obtained are 30 mg of 5-keto-14-hydroxy-$\Delta^{15,16}$-milbemycin D with a melting point of 170°–174° C.

Example S3: Preparation of 5-keto-$\Delta^{14,29}$-15-hydroxymilbemycin D (formula IX) and 5-keto-14-hydroxy-$\Delta^{15,16}$-milbemycin D from milbemycin D The oxidation with manganese dioxide as follow-up reaction of $\Delta^{14,29}$-15-hydroxymilbemycin D and 14-hydroxy-$\Delta^{15,16}$milbemycin D obtained by the singulett oxygen oxidation of Example S1 affords, in quantitative yield, 5-keto-$\Delta^{14,29}$-15-hydroxymilbemycin D and 5-keto-14-hydroxy-$\Delta^{15,16}$-milbemycin D respectively.

Example S4: Preparation of 5-acetyloxy-$\Delta^{14,29}$-15-hydroxymilbemycin D (formula IX) and 5-acetyloxy-14-hydroxy-$\Delta^{15,16}$-milbemycin D from milbemycin D (a) Preparation of 5-acetyloxymilbemycin D 160 mg (1.6 mM) of acetic anhydride are added to 560 g (1.0 mM) of milbemycin D in 20 ml of pyridine, and the mixture is stirred at room temperature overnight. The pyridine is evaporated off, and the residue is taken up in 20 ml of ethyl acetate. The organic phase is shaken once with 10 ml of a 1N solution of hydrochloric acid and then with 10 ml of a saturated solution of NaHCO$_3$ and finally with 10 ml of a concentrated solution of NaCl. The organic phase is separated and dried over Na$_2$SO$_4$, filtered and concentrated affording 580 mg of 5-acetyloxymilbemycin D as an amorphous, slightly yellow powder with a melting point of 115°–120° C.

The acyl derivatives, milbemycin A$_3$, milbemycin A$_4$ and the 13-desoxyavermectin derivative (R$_2$=sec-butyl) can also be prepared in analogous manner.

(b) 560 mg of 5-acetyloxymilbemycin D and 20 g of methylene blue in 40 ml of acetonitrile are treated with oxygen for 8 hours at 18°–22° C. in an irradiation apparatus (200 watt projector lamp). The reaction mixture is then reduced with 40 mg of triphenylphosphine at room temperature. The reaction mixture is concentrated, and the residue is chromatographed through a column of silica gel eluted with a 3:1 mixture of methylene chloride and ethyl acetate, affording 390 mg of 5-acetyloxy-$\Delta^{14,29}$-15-hydroxymilbemycin D with a melting point of 153°–156° C.; mass spectrum m/e: 614 (M+), 596. Also obtained are 42 mg of 5-acetyloxy-14-hydroxy-$\Delta^{15,16}$-milbemycin D with a melting point of 151°–154° C.

Example S5: Preparation of $\Delta^{14,29}$-15-hydroxymilbemycin A$_4$ (formula IX) and 14-hydroxy-$\Delta^{15,16}$-milbemycin A$_4$ from milbemycin A$_4$ 540 mg (1 mM) of milbemycin A$_4$ in 100 ml of acetonitrile are oxidised with singulett oxygen in accordance with Example S1 and subsequently reduced with triphenylphosphine. Purification by flash chromatography through silica gel eluted with a 1:1 mixture of cyclohexane and ethyl acetate yields 310 mg of $\Delta^{14,29}$-15-hydroxymilbemycin A$_4$ with a melting point of 222°–225° C.; mass spectrum m/e: 558 (M+), 540.

Also obtained are 40 mg of 14-hydroxy-$^{15,16}$-milbemycin A$_4$ with a melting point of 147°–152° C.; mass spectrum m/e: 558 (M+), 540.

Example S6: Preparation of 5-dimethyl-tert-butylsilyloxy-$\Delta^{14,29}$-15-hydroxymilbemycin A$_3$ (formula IX) and 5-dimethyl-tert-butylsilyl-14-hydroxy-$\Delta^{14,15}$-milbemycin A$_3$ from milbemycin A$_3$ (a) Preparation of 5-dimethyl-tert-butylsilylmilbemycin A$_3$ A reaction vessel is charged at room temperature with 480 mg (7 mM) of imidazole and 460 mg (3 mM) of dimethyl tert-butylchlorosilane in 20 ml of methylene chloride. With stirring, a solution of 655 mg (1.2 mM) of milbemycin A$_3$ in 10 ml of methylene chloride is slowly added dropwise, and the reaction mixture is heated overnight under reflux ($\sim$40° C.). The reaction mixture is concentrated, and the residue is purified through silica gel and dried, affording 730 mg of amorphous 5-dimethyl-tert-butylsilylmilbemycin A$_3$ with a melting point of 55°–60° C.

Milbemycin A$_4$, milbemycin D and the 13-desoxyavemectin derivative (R$_2$=sec-butyl) can be silylated in the same manner. Methyldiphenylchlorosilane or bis(isopropyl)methylchlorosilane can also be used with advantage in this reaction.

(b) In accordance with the procedure described in Example S4b), 550 mg of 5-dimethyl-tert-butylsilyl-$\Delta^{14,29}$-15-hydroxymilbemycin A$_3$ (m.p. 238°–240° C.; mass spectrum m/e: 658 (M+), 640) can be obtained from 720 mg of 5-dimethyl-tert-butylsilylmilbemycin A$_3$ by singulett oxygen oxidation with Bengal pink as sensitiser, and subsequent reaction of the peroxides with triphenylphosphine.

Also obtained are 42 mg of amorphous 5-dimethyl-tert-butylsilyl-14-hydroxy-$\Delta^{15,16}$-milbemycin A$_3$ with a melting point of 45°–50° C.

Example S7: Preparation of $\Delta^{14,29}$-15-hydroxymilbemycin A$_3$ (formula IX) and 14-hydroxy-$\Delta^{15,16}$-milbemycin A$_3$ 120 mg of 5-dimethyl-tert-butylsilyl-$\Delta^{14,29}$-15-hydroxymilbemycin A$_3$ and 2 ml of a 1% solution of p-toluenesulfonic acid in methanol are stirred for 9 hours at room temperature and then treated with a 5% aqueous solution of NaHCO$_3$. After extraction with three 2 ml portions of diethyl ether, the organic phase is concentrated and the crude product is chromatographed through 20 g of silica gel eluted with a 1:12 mixture of acetone and methylene chloride, affording 67 mg of $\Delta^{14,29}$-15-hydroxymilbemycin A$_3$ with a melting point of 219°–222° C.

In corresponding manner, 38 mg of 14-hydroxy-$\Delta^{15,16}$-milbemycin A$_3$ (m.p. 128°–132° C.) are obtained from 60 mg of 5-dimethyl-tert-butylsilyloxy-14-hydroxy-$\Delta^{15,16}$-milbemycin A$_3$.

Example S8: Preparation of 29-oxo-5-acetyloxy-$\Delta^{14,15\text{-}trans}$-milbemycin D (formula X) and 15-oxo-5-acetyloxy-$\Delta^{14,29}$-milbemycin D (formula XI)

570 mg of pyridinium dichromate are added at 10° C. to 600 mg of 15-hydroxy-5-acetyloxy-$\Delta^{14,29}$-milbemycin D in 35 ml of absolute dimethylformamide, and the batch is vigorously stirred for 2 hours at room temperature. The solvent is removed under a high vacuum, the resultant resin is suspended in diethyl ether, and the suspension is filtered. The liquid phase is washed with water and a saturated solution of sodium chloride, dried over sodium sulfate and filtered. The yellowish crude product is purified by chromatography through a column of silica gel eluted with a 15:1 mixture of methylene chloride and diethyl ether, affording 330 mg of 29-oxo-5-acetyloxy-$\Delta^{14,15}$-milbemycin D with a melting point of 155°-159° C. and, as by-product, 200 mg of 15-oxo-5-acetyloxy-$\Delta^{14,29}$-milbemycin D with a melting point of 139°-142° C.

Example S9: Preparation of 29-oxo-$\Delta^{14,15cis}$-milbemycin D (formula X) and 29-oxo-$\Delta^{14,15trans}$-milbemycin D (formula X)

136 mg of 29-oxo-$\Delta^{14,15trans}$-5-dimethyl-tert-butylsilyloxymilbemycin D are dissolved at room temperature in 15 ml of methanol. After the addition of 2 ml of p-toluenesulfonic acid, the batch is stirred for 1 hour. The solvent is subsequently removed under a high vacuum, and the crude product is purified by chromatography through a column of silica gel eluted with a 3:1 mixture of methylene chloride and diethyl ether, affording 125 mg of the trans-product in the form of a white amorphous powder with a melting point of about 150° C. Half of this trans-product is dissolved in methanol, and several drops of dilute sulfuric acid are added. After stirring for 3 hours at about 30° C., the solvent is removed under a high vacuum, and the crude product is dissolved in methylene chloride. The resultant solution is filtered through a short column (5 cm long) of silica gel, thus affording 60 mg of the more stable cis-product, which decomposes at about 250° C.

Example S10:

(a) Preparation of 29-hydroxy-$\Delta^{14,15cis}$-milbemycin D (formula II)

95 mg of 29-oxo-$\Delta^{14,15cis}$-milbemycin D are dissolved in 5 ml of methanol. With stirring, 10 mg of sodium borohydride are added at room temperature to the resultant solution. 30 minutes later 30 ml of methylene chloride are added. The solution is washed with 30 ml of water, dried over sodium sulfate and concentrated by evaporation. The crude product is purifed by chromatography through a column of silica gel eluted with a 2:1 mixture of methylene chloride and diethyl ether. Yield: 85 mg; m.p.: 160°-165° C.

(b) Preparation of 29-hydroxy-$\Delta^{14,15trans}$-milbemycin D (formula II)

14 mg of sodium borohydride are added at room temperature to 136 mg of 29-oxo-5-dimethyl-tert-butylsilyloxymilbemycin D in 10 ml of methanol. Working up as in Example S8 affords 120 mg of 29-hydroxy-$\Delta^{14,15trans}$-5-dimethyl-tert-butylsilyloxymilbemycin D with a melting point of 140°-145° C.

100 mg of this silyl derivative are dissolved at room temperature in 5 ml of methanol, followed by the addition of 2 mg of p-toluenesulfonic acid. 30 minutes later the solvent is removed under a high vacuum, and the residue is then purifed by chromatography through a column of silica gel eluted with a mixture of methylene chloride and diethyl ether, affording 65 mg of 29-hydroxy-$\Delta^{14,15trans}$-milbemycin D with a melting point of 153°-158° C.

Example S11: Preparation of 15-mesyloxy-$\Delta^{14,29}$-5-dimethyl-tert-butylsilyloxymilbemycin A$_4$ Under argon, 230 mg (2 mM) of methane sulfochloride in 2 ml of tetrahydrofuran are added at about $-10°$ C. to a solution of 670 mg (1 mM) of 15-hydroxy-$\Delta^{14,29}$-5-dimethyl-tert-butylsilyloxymilbemycin A$_4$ and 405 mg (4 mM) of triethylamine in 40 ml of dry tetrahydrofuran. With vigorous stirring, the solution is slowly heated to about $+10°$ C. and stirred further for 30 minutes. This intermediate prepared in situ can be further processed without purification.

Example S12: Preparation of 29-hydroxy-5-dimethyl-tert-butylsilyloxymilbemycin A$_4$ About 5.4 ml (300 mM) of water are added at about 10° C. to the A$_4$-derivative prepared in accordance with the previous Example S11, in the tetrahydrofuran reaction mixture, and the batch is stirred overnight at room temperature.

200 ml of ethyl acetate are added, and the batch is then extracted with a saturated solution of sodium chloride. After drying over a suitable drying agent, e.g. sodium sulfate, the solvent is removed in vacuo. Purification through a column of silica gel eluted with a 20:1 mixture of methylene chloride and diethyl ether affords, after freeze drying, 470 mg of the title substance with a melting point of 142°-145° C.

Example S13: Preparation of 29-hydroxymilbemycin A$_4$

If in the previous Example S12, either before or after the addition of water, the reaction mixture is acidified with p-toluenesulfonic acid or methanesulfonic acid, then this affords the title compound, which, after freeze drying, melts at 143°-147° C.

Example S14: Preparation of 5,15-bisacetyloxy-$\Delta^{14,29}$-milbemycin D

With good stirring, 100 mg (1.27 mM) of acetyl chloride in 3 ml of methylene chloride are added at about 10° C. to a solution of 290 mg (0.5 mM) of 15-hydroxy-$\Delta^{14,29}$-milbemycin D and 100 mg (1.26 mM) of pyridine in 30 ml of methylene chloride, and the batch is subsequently stirred overnight at about 35° C. The batch is then diluted with 100 ml of ethyl acetate, and the resultant solution is extracted with 0.5N hydrochloric acid and then with a solution of sodium chloride. Purification through a column of silica gel eluted with a 2:1 mixture of methylene chloride and ether affords 275 mg of a white powder which decomposes at 227°-231° C.

$^1$H-NMR (250 MHz, CDCl$_3$): 3.03 ppm (br.d.; 8 Hz) (C$_{25}$—H); 4.96 ppm (AB-system); 2.16 ppm and 2.20 ppm (2 acetyl).

Mass spectrum (FD) m/e 656 (M$^+$, C$_{37}$H$_{52}$O$_{10}$).

PREPARATION OF THE FINAL PRODUCTS

Example F1: Preparation of 29-acetoxymilbemycin A$_4$

Under nitrogen, 76 mg (0.44 mM) of methanesulfonic acid anhydride are added at about $-10°$ C. to a solution of 150 mg (0.22 mM) of 15-hydroxy-$\Delta^{14,29}$-5-dimethyl-tert-butylsilyloxymilbemycin A$_4$, 89 mg (0.88 mM) of triethylamine and 1 mg of p-dimethylaminopyridine in 30 ml of dry tetrahydrofuran. With good stirring, the solution is slowly heated to room temperature and then stirred further for about half an hour. 2.64 g (44 mM) of glacial acetic acid are then added, and the batch is stirred for 24 hours at 60° C.

After the usual working up, 35 mg of the title substance are obtained in the form of a white amorphous powder with a melting point of 73°-76° C.

¹H-NMR (300 MHz, CDCl₃): 5.22 ppm (dd; 5 and 10 Hz) $C_{15}$—H); 3.05 ppm (dt; 3 and 10 Hz) $C_{25}$—H); 4.51 ppm (AB-system) ($C_{29}$—H₂).

Mass spectrum (FD) m/e 600 (M+, $C_{34}H_{48}O_9$).

Example F2: Preparation of 29-cyclopropanecarbonyloxymilbemycin A₄

A solution of 300 mg (0.45 mM) of 29-hydroxy-5-dimethyl-tert-butylsilyloxymilbemycin A₄, 95 mg (0.9 mM) of cyclopropanoyl chloride, 180 mg (1.8 mM) of triethylamine and about 5 mg of p-dimethylaminopyridine in 30 ml of dry tetrahydrofuran is stirred under reflux for 2 hours. The solvent is evaporated off, the residue is taken up in 100 ml of ethyl acetate, and the solution formed is extracted with water. After drying over sodium sulfate, the organic phase is distilled off. The resultant crude 29-cyclopropanoyl-5-O-(dimethyl-tert-butylsilyloxy)milbemycin A₄ is taken up in 20 ml of methanol containing 1% of p-toluenesulfonic acid, and the solution formed is stirred for 1 hour at room temperature. After the solvent has been distilled off, the residue is purified through a column of silica eluted with a 2:1 mixture of diethyl ether and hexane. After freeze drying, 188 mg of 29-cyclopropanoylmilbemycin A₄ are obtained in the form of a white amorphous powder with a melting point of 103°-107° C.

¹H-NMR (300 MHz, CDCl₃): 5.12 ppm (dd; 5 and 10 Hz) ($C_{15}$—H); 3.05 ppm (dt; 2 and 10 Hz) ($C_{25}$—H); 4.52 ppm (AB-system) ($C_{29}$—H₂).

Mass spectrum (FD) m/e 626 (M+, $C_{36}H_{50}O_9$).

Example F3: Preparation of 29-tert-butylcarbonyloxymilbemycin D

A solution of 690 mg (1 mM) of 29-hydroxy-5-dimethyl-tert-butylsilyloxymilbemycin D, 560 mg (3 mM) of pivaloyl anhydride and about 5 mg of p-dimethylaminopyridine in 30 ml of pyridine is stirred for 2 hours at 90° C. After the solvent has been distilled off, the residue is taken up in 20 ml of methanol containing 1% of p-toluenesulfonic acid, and the solution formed is stirred for 1 hour at room temperature. The solvent is distilled off, and the resultant crude product is purified by chromatography through a column of silica eluted with a 4:1 mixture of methylene chloride and diethyl ether, affording 605 g of the title substance in the form of a white amorphous powder with a melting point of 75°-80° C.

¹H-NMR (300 MHz, CDCl₃): 5.10 ppm (dd; 3 and 11 Hz) ($C_{15}$—H); 2.94 ppm (dd; 1 and 8 Hz) ($C_{25}$—H); 4.42 ppm (AB-system) ($C_{29}$—H₂).

Mass spectrum (FD) m/e 656 (M+, $C_{38}H_{56}O_9$).

Example F4: Preparation of 5-oximino-29-tert-butylcarbonyloxymilbemycin A₄

With the simultaneous addition of 2.0 g of molecular sieve, a solution of 220 mg (0.34 mM) of 5-keto-29-tert-butylcarbonyloxymilbemycin A₄, 30 ml of methanol, 10 ml of tetrahydrofuran and 300 mg (4.3 mM) of hydroxylamine hydrochloride is stirred thoroughly overnight at room temperature. After filtration, the solvent is evaporated off in vacuo, and the residue is purifed by chromatography through a column of silica gel eluted with a 10:1 mixture of methylene chloride and diethyl ether, affording 192 mg of the amorphous title substance, which, after freeze drying, melts at 145°-150° C.

The following compounds are prepared by procedures analogous to those described above:

TABLE 1

Typical representatives of intermediates of formula II
[ = $\Delta^{14,15 trans}$-29-hydroxy]

| Comp. | R₂ | X | m.p. [°C.] |
|---|---|---|---|
| 1.1 | CH₃ | —C(O)— | |
| 1.2. | C₂H₅ | —C(O)— | |
| 1.3. | C₃H₇-iso | —C(O)— | |
| 1.4. | C₄H₉-sec | —C(O)— | |
| 1.5. | CH₃ | —C(OH)— | |
| 1.6. | C₂H₅ | —C(OH)— | 143–147 |
| 1.7. | C₃H₇-iso | —C(OH)— | 153–158 |
| 1.8. | CH₄H₉-sec | —C(OH)— | |
| 1.9. | CH₃ | —C[OSi(CH₃)₂C₄H₉-tert] | |
| 1.10 | C₂H₅ | —C[OSi(CH₃)₂C₄H₉-tert] | 142–145 |
| 1.11 | C₃H₇-iso | —C[OSi(CH₃)₂C₄H₉-tert] | 140–145 |
| 1.12 | C₄H₉-sec | —C[OSi(CH₃)₂C₄H₉-tert] | |
| 1.13 | CH₃ | —C[OC(O)CH₃] | |
| 1.14 | C₂H₅ | —C[OC(O)CH₃] | |
| 1.15 | C₃H₇-iso | —C[OC(O)CH₃] | 144–147 |
| 1.16 | C₄H₉-tert | —C[OC(O)CH₃] | |

This list constitutes no limitation.

TABLE 2

Typical representatives of intermediates of formula II
[ = $\Delta^{14,15 cis}$-29-hydroxy]

| Comp. | R₂ | X | m.p. [°C.] |
|---|---|---|---|
| 2.1 | CH₃ | —C(O)— | |
| 2.2. | C₂H₅ | —C(O)— | |
| 2.3. | C₃H₇-iso | —C(O)— | |
| 2.4. | C₄H₉-sec | —C(O)— | |
| 2.5. | CH₃ | —C(OH)— | |
| 2.6. | C₂H₅ | —C(OH)— | |
| 2.7. | C₃H₇-iso | —C(OH)— | 160–165 |
| 2.8. | C₄H₉-sec | —C(OH)— | |
| 2.9. | CH₃ | —C[OSi(CH₃)₂C₄H₉-tert] | |
| 2.10 | C₂H₅ | —C[OSi(CH₃)₂C₄H₉-tert] | |
| 2.11 | C₃H₇-iso | —C[OSi(CH₃)₂C₄H₉-tert] | |
| 2.12 | C₄H₉-sec | C[OSi(CH₃)₂C₄H₉-tert] | |
| 2.13 | CH₃ | —C[OC(O)CH₃] | |
| 2.14 | C₂H₅ | —C[OC(O)CH₃] | |
| 2.15 | C₃H₇-iso | —C[OC(O)CH₃] | |
| 2.16 | C₄H₉-tert | —C[OC(O)CH₃] | |

This list constitutes no limitation.

TABLE 3

Typical representatives of intermediates of formula X
[ = $\Delta^{14,15 trans}$-29-oxo]

| Comp. | R₂ | X | m.p. [°C.] |
|---|---|---|---|
| 3.1 | CH₃ | —C(O)— | |
| 3.2. | C₂H₅ | —C(O)— | 115–118 |
| 3.3. | C₃H₇-iso | —C(O)— | 120–125 |
| 3.4. | C₄H₉-sec | —C(O)— | |
| 3.5. | CH₃ | —C(OH)— | |
| 3.6. | C₂H₅ | —C(OH)— | |
| 3.7. | C₃H₇-iso | —C(OH)— | 120–124 |
| 3.8. | CH₄H₉-sec | —C(OH)— | |
| 3.9. | CH₃ | —C[OSi(CH₃)₂C₄H₉-tert] | |
| 3.10 | C₂H₅ | —C[OSi(CH₃)₂C₄H₉-tert] | 250–253 |
| 3.11 | C₃H₇-iso | —C[OSi(CH₃)₂C₄H₉-tert] | 215–220 |
| 3.12 | C₄H₉-sec | —C[OSi(CH₃)₂C₄H₉-tert] | |
| 3.13 | CH₃ | —C[OC(O)CH₃] | |
| 3.14 | C₂H₅ | —C[OC(O)CH₃] | |
| 3.15 | C₃H₇-iso | —C[OC(O)CH₃] | 155–159 |
| 3.16 | C₄H₉-tert | —C[OC(O)CH₃] | |

This list constitutes no limitation.

TABLE 4

Typical representatives of intermediates of formula X
$[= \Delta^{14,29cis}\text{-}29\text{-}oxo]$

| Comp. | $R_2$ | X | m.p. [°C.] |
|---|---|---|---|
| 4.1 | $CH_3$ | —C(O)— | |
| 4.2 | $C_2H_5$ | —C(O)— | |
| 4.3 | $C_3H_7$-iso | —C(O)— | |
| 4.4 | $C_4H_9$-sec | —C(O)— | |
| 4.5 | $CH_3$ | —C(OH)— | |
| 4.6 | $C_2H_5$ | —C(OH)— | amorphous ca. 60 |
| 4.7 | $C_3H_7$-iso | —C(OH)— | decomp. from 250 |
| 4.8 | $C_4H_9$-sec | —C(OH)— | |
| 4.9 | $CH_3$ | —C[OSi$(CH_3)_2C_4H_9$-tert] | |
| 4.10 | $C_2H_5$ | —C[OSi$(CH_3)_2C_4H_9$-tert] | 212–215 |
| 4.11 | $C_3H_7$-iso | —C[OSi$(CH_3)_2C_4H_9$-tert] | 78–83 |
| 4.12 | $C_4H_9$-sec | —C[OSi$(CH_3)_2C_4H_9$-tert] | |
| 4.13 | $CH_3$ | —C[OC(O)$CH_3$] | |
| 4.14 | $C_2H_5$ | —C[OC(O)$CH_3$] | |
| 4.15 | $C_3H_7$-iso | —C[OC(O)$CH_3$] | |
| 4.16 | $C_4H_9$-tert | —C[OC(O)$CH_3$] | |

This list constitutes no limitation.

TABLE 5

Typical representatives of compounds of formula I wherein X is —C(OH)—:

| Comp. | $R_2$ | R | Physical data m.p. [°C.] |
|---|---|---|---|
| 5.1 | $CH_3$ | H | |
| 5.2 | $C_2H_5$ | H | |
| 5.3 | $C_3H_7$-iso | H | |
| 5.4 | $C_4H_9$-sec | H | |
| 5.5 | $CH_3$ | $CH_3$ | |
| 5.6 | $C_2H_5$ | $CH_3$ | 73–76 |
| 5.7 | $C_3H_7$-iso | $CH_3$ | |
| 5.8 | $C_4H_9$-sec | $CH_3$ | |
| 5.9 | $CH_3$ | $C(CH_3)_3$ | |
| 5.10 | $C_2H_5$ | $C(CH_3)_3$ | 110–115 |
| 5.11 | $C_3H_7$-iso | $C(CH_3)_3$ | 75–80 |
| 5.12 | $C_4H_9$-sec | $C(CH_3)_3$ | |
| 5.13 | $CH_3$ | $CH_3OCH_2$ | |
| 5.14 | $C_2H_5$ | $CH_3OCH_2$ | |
| 5.15 | $C_3H_7$-iso | $CH_3OCH_2$ | |
| 5.16 | $C_4H_9$-sec | $CH_3OCH_2$ | |
| 5.17 | $CH_3$ | $CH_3O(CH_3)_2C$ | |
| 5.18 | $C_2H_5$ | $CH_3O(CH_3)_2C$ | |
| 5.19 | $C_3H_7$-iso | $CH_3O(CH_3)_2C$ | |
| 5.20 | $C_4H_4$-sec | $CH_3O(CH_3)_2C$ | |
| 5.21 | $CH_3$ | $(CH_3)_2CH-CH_2$ | |
| 5.22 | $C_2H_5$ | $(CH_3)_2CH-CH_2$ | 95–100 |
| 5.23 | $C_3H_7$-iso | $(CH_3)_2CH-CH_2$ | |
| 5.24 | $C_4H_9$-sec | $(CH_3)_2CH-CH_2$ | |
| 5.25 | $CH_3$ | $CCl_3$ | |
| 5.26 | $C_2H_5$ | $CCl_3$ | |
| 5.27 | $C_3H_7$-iso | $CCl_3$ | |
| 5.28 | $C_4H_9$-sec | $CCl_3$ | |
| 5.29 | $CH_3$ | $CF_3$ | |
| 5.30 | $C_2H_5$ | $CF_3$ | |
| 5.31 | $C_3H_7$-iso | $CF_3$ | |
| 5.32 | $C_4H_9$-sec | $CF_3$ | |
| 5.33 | $CH_3$ | $Cl_3CCHCl$ | |
| 5.34 | $C_2H_5$ | $Cl_3CCHCl$ | |
| 5.35 | $C_3H_7$-iso | $Cl_3CCHCl$ | |
| 5.36 | $C_4H_9$-sec | $Cl_3CCHCl$ | |
| 5.37 | $CH_3$ | $ClCH_2CH_2CH_2$ | |
| 5.38 | $C_2H_5$ | $ClCH_2CH_2CH_2$ | |
| 5.39 | $C_3H_7$-iso | $ClCH_2CH_2CH_2$ | |
| 5.40 | $C_4H_9$-sec | $ClCH_2CH_2CH_2$ | |
| 5.41 | $CH_3$ | $CH_2=CH$ | |
| 5.42 | $C_2H_5$ | $CH_2=CH$ | |
| 5.43 | $C_3H_7$-iso | $CH_2=CH$ | |
| 5.44 | $C_4H_9$-sec | $CH_2=CH$ | |
| 5.45 | $CH_3$ | $CH_2=CH-CH_2$ | |
| 5.46 | $C_2H_5$ | $CH_2=CH-CH_2$ | |
| 5.47 | $C_3H_7$-iso | $CH_2=CH-CH_2$ | |
| 5.48 | $C_5H_9$-sec | $CH_2=CH-CH_2$ | |
| 5.49 | $CH_3$ | $CH=C-CH_2$ | |
| 5.50 | $C_2H_5$ | $CH=C-CH_2$ | |
| 5.51 | $C_3H_7$-iso | $CH=C-CH_2$ | |
| 5.52 | $C_4H_9$-sec | $CH=C-CH_2$ | |
| 5.53 | $CH_3$ | $(CH_3)_2C=CH$ | |
| 5.54 | $C_2H_5$ | $(CH_3)_2C=CH$ | |
| 5.55 | $C_3H_7$-iso | $(CH_3)_2C=CH$ | |
| 5.56 | $C_4H_9$-sec | $(CH_3)_2C=CH$ | |
| 5.57 | $CH_3$ | $(Cl)_2C=C(Cl)$ | |
| 5.58 | $C_2H_5$ | $(Cl)_2C=C(Cl)$ | |
| 5.59 | $C_3H_7$-iso | $(Cl)_2C=C(Cl)$ | |
| 5.60 | $C_4H_9$-sec | $(Cl)_2C=C(Cl)$ | |
| 5.61 | $CH_3$ | $CF_3CCl_2$ | |
| 5.62 | $C_2H_5$ | $CF_3CCl_2$ | |
| 5.63 | $C_3H_7$-iso | $CF_3CCl_2$ | |
| 5.64 | $C_4H_9$-sec | $CF_3CCl_2$ | |
| 5.65 | $CH_3$ | cyclopropyl | |
| 5.66 | $C_2H_5$ | cyclopropyl | 103–108 |
| 5.67 | $C_3H_7$-iso | cyclopropyl | |
| 5.68 | $C_4H_9$-sec | cyclopropyl | |
| 5.69 | $CH_3$ | 2,2-dimethylcyclopropyl | |
| 5.70 | $C_2H_5$ | 2,2-dimethylcyclopropyl | |
| 5.71 | $C_3H_7$-iso | 2,2-dimethylcyclopropyl | |
| 5.72 | $C_4H_9$-sec | 2,2-dimethylcyclopropyl | |
| 5.73 | $CH_3$ | 2,2-dimethyl-3-(2,2-dichlorovinyl)cyclopropyl | |
| 5.74 | $C_2H_5$ | 2,2-dimethyl-3-(2,2-dichlorovinyl)cyclopropyl | |
| 5.75 | $C_3H_7$-iso | 2,2-dimethyl-3-(2,2-dichlorovinyl)cyclopropyl | |
| 5.76 | $C_4H_9$-sec | 2,2-dimethyl-3-(2,2-dichlorovinyl)cyclopropyl | |
| 5.77 | $CH_3$ | cyclobutyl | |
| 5.78 | $C_2H_5$ | cyclobutyl | |
| 5.79 | $C_3H_7$-iso | cyclobutyl | |
| 5.80 | $C_4H_9$-sec | cyclobutyl | |
| 5.81 | $C_3$ | cyclohexyl | |
| 5.82 | $C_2H_5$ | cyclohexyl | |
| 5.83 | $C_3H_7$-iso | cyclohexyl | |
| 5.84 | $C_4H_9$-sec | cyclohexyl | |
| 5.85 | $CH_3$ | phenyl | |
| 5.86 | $C_2H_5$ | phenyl | |
| 5.87 | $C_3H_7$-iso | phenyl | |
| 5.88 | $C_4H_9$-sec | phenyl | |
| 5.89 | $CH_3$ | p-chlorophenyl | |
| 5.90 | $C_2H_5$ | p-chlorophenyl | |
| 5.91 | $C_3H_7$-iso | p-chlorophenyl | |
| 5.92 | $C_4H_9$-sec | p-chlorophenyl | |
| 5.93 | $CH_3$ | p-tolyl | |
| 5.94 | $C_3H_5$ | p-tolyl | |
| 5.95 | $C_3H_7$-iso | p-tolyl | |
| 5.96 | $C_4H_9$-sec | p-tolyl | |
| 5.97 | $CH_3$ | p-nitrophenyl | |
| 5.98 | $C_2H_5$ | p-nitrophenyl | 125–130 |
| 5.99 | $C_3H_7$-iso | p-nitrophenyl | |
| 5.100 | $C_4H_9$-sec | p-nitrophenyl | |
| 5.101 | $CH_3$ | $(CH_3)_3C-CH_2$ | |
| 5.102 | $C_2H_5$ | $(CH_3)_3C-CH_2$ | 103–105 |
| 5.103 | $C_3H_7$-iso | $(CH_3)_3C-CH_2$ | |
| 5.104 | $C_4H_9$-sec | $(CH_3)_3C-CH_2$ | |
| 5.105 | $CH_3$ | m-chlorophenyl | |
| 5.106 | $C_2H_5$ | m-chlorophenyl | 110–115 |
| 5.107 | $C_3H_7$-iso | m-chlorophenyl | |
| 5.108 | $C_4H_9$-sec | m-chlorophenyl | |
| 5.109 | $CH_3$ | p-methoxyphenyl | |
| 5.110 | $C_2H_5$ | p-methoxyphenyl | 105–110 |
| 5.111 | $C_3H_7$-iso | p-methoxyphenyl | |
| 5.112 | $C_4H_9$-sec | p-methoxyphenyl | |
| 5.113 | $CH_3$ | 2,6-difluorophenyl | |
| 5.114 | $C_3H_5$ | 2,6-difluorophenyl | 107–111 |
| 5.115 | $C_3H_7$-iso | 2,6-difluorophenyl | |
| 5.116 | $C_4H_9$-sec | 2,6-difluorophenyl | |

The contents of this Table are of illustrative nature and constitute no limitation.

TABLE 6

Typical representatives of compounds of formula I wherein X is $-CH[OSi(CH_3)_2C_4H_9-t]$:

| Comp. | $R_2$ | R | Physical data m.p. [°C.] |
|---|---|---|---|
| 6.1 | $CH_3$ | H | |
| 6.2 | $C_2H_5$ | H | |
| 6.3 | $C_3H_7$-iso | H | |
| 6.4 | $C_4H_9$-sec | H | |
| 6.5 | $CH_3$ | $CH_3$ | |
| 6.6 | $C_2H_5$ | $CH_3$ | |
| 6.7 | $C_3H_7$-iso | $CH_3$ | 78–83 |
| 6.8 | $C_4H_9$-sec | $CH_3$ | |
| 6.9 | $CH_3$ | $C(CH_3)_3$ | |
| 6.10 | $C_2H_5$ | $C(CH_3)_3$ | 65–70 |
| 6.11 | $C_3H_7$-iso | $C(CH_3)_3$ | 86–90 |
| 6.12 | $C_4H_9$-sec | $C(CH_3)_3$ | |
| 6.13 | $CH_3$ | $CH_3OCH_2$ | |
| 6.14 | $C_2H_5$ | $CH_3OCH_2$ | |
| 6.15 | $C_3H_7$-iso | $CH_3OCH_2$ | |
| 6.16 | $C_4H_9$-sec | $CH_3OCH_2$ | |
| 6.17 | $CH_3$ | $CH_3O(CH_3)_2C$ | |
| 6.18 | $C_2H_5$ | $CH_3O(CH_3)_2C$ | |
| 6.19 | $C_3H_7$-iso | $CH_3O(CH_3)_2C$ | |
| 6.20 | $C_4H_9$-sec | $CH_3O(CH_3)_2C$ | |
| 6.21 | $CH_3$ | $(CH_3)_2CH-CH_2$ | |
| 6.22 | $C_2H_5$ | $(CH_3)_2CH-CH_2$ | 65–70 |
| 6.23 | $C_3H_7$-iso | $(CH_3)_2CH-CH_2$ | |
| 6.24 | $C_4H_9$-sec | $(CH_3)_2CH-CH_2$ | |
| 6.25 | $CH_3$ | $CCl_3$ | |
| 6.26 | $C_2H_5$ | $CCl_3$ | |
| 6.27 | $C_3H_7$-iso | $CCl_3$ | |
| 6.28 | $C_4H_9$-sec | $CCl_3$ | |
| 6.29 | $CH_3$ | $CF_3$ | |
| 6.30 | $C_2H_5$ | $CF_3$ | |
| 6.31 | $C_3H_7$-iso | $CF_3$ | |
| 6.32 | $C_4H_9$-sec | $CF_3$ | |
| 6.33 | $CH_3$ | $Cl_3CCHCl$ | |
| 6.34 | $C_2H_5$ | $Cl_3CCHCl$ | |
| 6.35 | $C_3H_7$-iso | $Cl_3CCHCl$ | |
| 6.36 | $C_4H_9$-sec | $Cl_3CCHCl$ | |
| 6.37 | $CH_3$ | $ClCH_2CH_2CH_2$ | |
| 6.38 | $C_2H_5$ | $ClCH_2CH_2CH_2$ | |
| 6.39 | $C_3H_7$-iso | $ClCH_2CH_2CH_2$ | |
| 6.40 | $C_4H_9$-sec | $ClCH_2CH_2CH_2$ | |
| 6.41 | $CH_3$ | $CH_2=CH$ | |
| 6.42 | $C_2H_5$ | $CH_2=CH$ | |
| 6.43 | $C_3H_7$-iso | $CH_2=CH$ | |
| 6.44 | $C_4H_9$-sec | $CH_2=CH$ | |
| 6.45 | $CH_3$ | $CH_2=CH-CH_2$ | |
| 6.46 | $C_2H_5$ | $CH_2=CH-CH_2$ | |
| 6.47 | $C_3H_7$-iso | $CH_2=CH-CH_2$ | |
| 6.48 | $C_4H_9$-sec | $CH_2=CH-CH_2$ | |
| 6.49 | $CH_3$ | $CH=C-CH_2$ | |
| 6.50 | $C_2H_5$ | $CH=C-CH_2$ | |
| 6.51 | $C_3H_7$-iso | $CH=C-CH_2$ | |
| 6.52 | $C_4H_9$-sec | $CH=C-CH_2$ | |
| 6.53 | $CH_3$ | $(CH_3)_2C=CH$ | |
| 6.54 | $C_2H_5$ | $(CH_3)_2C=CH$ | |
| 6.55 | $C_3H_7$-iso | $(CH_3)_2C=CH$ | |
| 6.56 | $C_4H_9$-sec | $(CH_3)_2C=CH$ | |
| 6.57 | $CH_3$ | $(Cl)_2C=C(Cl)$ | |
| 6.58 | $C_2H_5$ | $(Cl)_2C=C(Cl)$ | |
| 6.59 | $C_3H_7$-iso | $(Cl)_2C=C(Cl)$ | |
| 6.60 | $C_4H_9$-sec | $(Cl)_2C=C(Cl)$ | |
| 6.61 | $CH_3$ | $CF_3CCl_2$ | |
| 6.62 | $C_2H_5$ | $CF_3CCl_2$ | |
| 6.63 | $C_3H_7$-iso | $CF_3CCl_2$ | |
| 6.64 | $C_4H_9$-sec | $CF_3CCl_2$ | |
| 6.65 | $CH_3$ | cyclopropyl | |
| 6.66 | $C_2H_5$ | cyclopropyl | 91–95 |
| 6.67 | $C_3H_7$-iso | cyclopropyl | |
| 6.68 | $C_4H_9$-sec | cyclopropyl | |
| 6.69 | $CH_3$ | 2,2-dimethyl-cyclopropyl | |
| 6.70 | $C_2H_5$ | 2,2-dimethyl-cyclopropyl | |
| 6.71 | $C_3H_7$-iso | 2,2-dimethyl-cyclopropyl | |
| 6.72 | $C_4H_9$-sec | 2,2-dimethyl-cyclopropyl | |
| 6.73 | $CH_3$ | 2,2-dimethyl-3-(2,2-dichlorovinyl)cyclopropyl | |
| 6.74 | $C_2H_5$ | 2,2-dimethyl-3-(2,2-dichlorovinyl)cyclopropyl | |
| 6.75 | $C_3H_7$-iso | 2,2-dimethyl-3-(2,2-dichlorovinyl)cyclopropyl | |
| 6.76 | $C_4H_9$-sec | 2,2-dimethyl-3-(2,2-dichlorovinyl)cyclopropyl | |
| 6.77 | $CH_3$ | cyclobutyl | |
| 6.78 | $C_2H_5$ | cyclobutyl | |
| 6.79 | $C_3H_7$-iso | cyclobutyl | |
| 6.80 | $C_4H_9$-sec | cyclobutyl | |
| 6.81 | $CH_3$ | cyclohexyl | |
| 6.82 | $C_2H_5$ | cyclohexyl | |
| 6.83 | $C_3H_7$-iso | cyclohexyl | |
| 6.84 | $C_4H_9$-sec | cyclohexyl | |
| 6.85 | $CH_3$ | phenyl | |
| 6.86 | $C_2H_5$ | phenyl | |
| 6.87 | $C_3H_7$-iso | phenyl | |
| 6.88 | $C_4H_9$-sec | phenyl | |
| 6.89 | $CH_3$ | p-chlorophenyl | |
| 6.90 | $C_2H_5$ | p-chlorophenyl | |
| 6.91 | $C_3H_7$-iso | p-chlorophenyl | |
| 6.92 | $C_4H_9$-sec | p-chlorophenyl | |
| 6.93 | $CH_3$ | p-tolyl | |
| 6.94 | $C_2H_5$ | p-tolyl | |
| 6.95 | $C_3H_7$-iso | p-tolyl | |
| 6.96 | $C_4H_9$-sec | p-tolyl | |
| 6.97 | $CH_3$ | p-nitrophenyl | |
| 6.98 | $C_2H_5$ | p-nitrophenyl | 120–125 |
| 6.99 | $C_3H_7$-iso | p-nitrophenyl | |
| 6.100 | $C_4H_9$-sec | p-nitrophenyl | |
| 6.101 | $CH_3$ | $(CH_3)_3C-CH_2$ | |
| 6.102 | $C_2H_5$ | $(CH_3)_3C-CH_2$ | 90–95 |
| 6.103 | $C_3H_7$-iso | $(CH_3)_3C-CH_2$ | |
| 6.104 | $C_4H_9$-sec | $(CH_3)_3C-CH_2$ | |
| 6.105 | $CH_3$ | m-chlorophenyl | |
| 6.106 | $C_2H_5$ | m-chlorophenyl | 103–106 |
| 6.107 | $C_3H_7$-iso | m-chlorophenyl | |
| 6.108 | $C_4H_9$-sec | m-chlorophenyl | |
| 6.109 | $CH_3$ | p-methoxyphenyl | |
| 6.110 | $C_2H_5$ | p-methoxyphenyl | 100–105 |
| 6.111 | $C_3H_7$-iso | p-methoxyphenyl | |
| 6.112 | $C_4H_9$-sec | p-methoxyphenyl | |
| 6.113 | $CH_3$ | 2,6-difluorophenyl | |
| 6.114 | $C_2H_5$ | 2,6-difluorophenyl | 108–110 |
| 6.115 | $C_3H_7$-iso | 2,6-difluorophenyl | |
| 6.116 | $C_4H_9$-sec | 2,6-difluorophenyl | |

The contents of this Table are of illustrative nature and constitute no limitation.

TABLE 7

Typical representatives of compounds of formula I wherein $R_1$ is the group

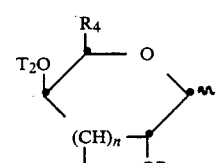

and $R_2$ is $CH_3$, $C_2H_5$, $C_3H_7$-iso or $C_4H_9$-sec and R is $CH_3$, $C_2H_5$, $C_3H_7$-i, $C_4H_9$-t, $(CH_3)_2CH-CH_2$ or $(CH_3)_3C-CH_2$ are:

| Comp. | $R_1$ |
|---|---|
| 7.1 | 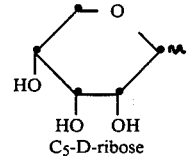 |
| | $C_5$-D-ribose |

TABLE 7-continued

Typical representatives of compounds of formula I wherein $R_1$ is the group

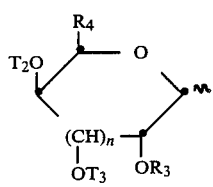

and $R_2$ is $CH_3$, $C_2H_5$, $C_3H_7$-iso or $C_4H_9$-sec and R is $CH_3$, $C_2H_5$, $C_3H_7$-i, $C_4H_9$-t, $(CH_3)_2CH-CH_2$ or $(CH_3)_3C-CH_2$ are:

| Comp. | $R_1$ |
|---|---|
| 7.2 | 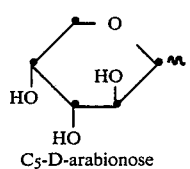 $C_5$-D-arabionose |
| 7.3 | 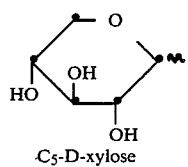 $C_5$-D-xylose |
| 7.4 | 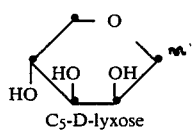 $C_5$-D-lyxose |
| 7.5 | 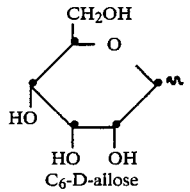 $C_6$-D-allose |
| 7.6 | 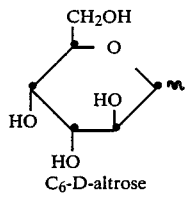 $C_6$-D-altrose |
| 7.7 | 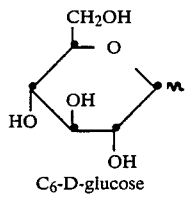 $C_6$-D-glucose |
| 7.8 | 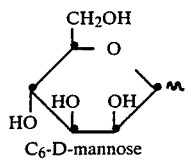 $C_6$-D-mannose |

TABLE 7-continued

Typical representatives of compounds of formula I wherein $R_1$ is the group

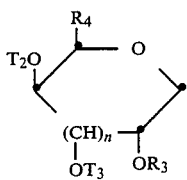

and $R_2$ is $CH_3$, $C_2H_5$, $C_3H_7$-iso or $C_4H_9$-sec and R is $CH_3$, $C_2H_5$, $C_3H_7$-i, $C_4H_9$-t, $(CH_3)_2CH-CH_2$ or $(CH_3)_3C-CH_2$ are:

| Comp. | $R_1$ |
|---|---|
| 7.9 | 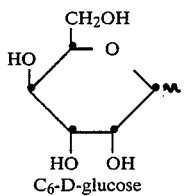 $C_6$-D-glucose |
| 7.10 | 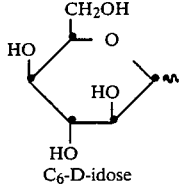 $C_6$-D-idose |
| 7.11 | 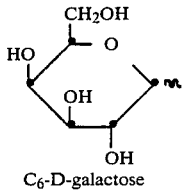 $C_6$-D-galactose |
| 7.12 | 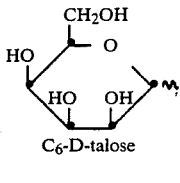 $C_6$-D-talose |
| 7.13 | 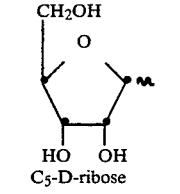 $C_5$-D-ribose |
| 7.14 | 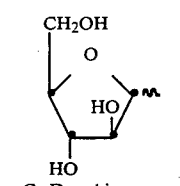 $C_5$-D-arabinose |

TABLE 7-continued

Typical representatives of compounds of formula I wherein $R_1$ is the group

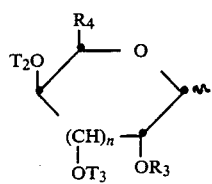

and $R_2$ is $CH_3$, $C_2H_5$, $C_3H_7$-iso or $C_4H_9$-sec and R is $CH_3$, $C_2H_5$, $C_3H_7$-i, $C_4H_9$-t, $(CH_3)_2CH-CH_2$ or $(CH_3)_3C-CH_2$ are:

| Comp. | $R_1$ |
|---|---|
| 7.15 | $C_5$-D-xylose |
| 7.16 | $C_5$-D-lyxose |
| 7.17 | $C_6$-D-allose |
| 7.18 | $C_6$-D-altrose |
| 7.19 | $C_6$-D-glucose |
| 7.20 | $C_6$-D-mannose |

TABLE 7-continued

Typical representatives of compounds of formula I wherein $R_1$ is the group

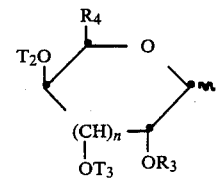

and $R_2$ is $CH_3$, $C_2H_5$, $C_3H_7$-iso or $C_4H_9$-sec and R is $CH_3$, $C_2H_5$, $C_3H_7$-i, $C_4H_9$-t, $(CH_3)_2CH-CH_2$ or $(CH_3)_3C-CH_2$ are:

| Comp. | $R_1$ |
|---|---|
| 7.21 | $C_6$-D-gulose |
| 7.22 | $C_6$-D-idose |
| 7.23 | $C_6$-D-galactose |
| 7.24 | $C_6$-D-talose |
| 7.25 | $C_6$-D-psicose |
| 7.26 | $C_6$-D-fructose |

TABLE 7-continued

Typical representatives of compounds of formula I wherein $R_1$ is the group

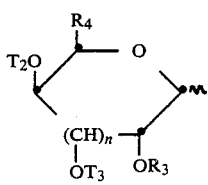

and $R_2$ is $CH_3$, $C_2H_5$, $C_3H_7$-iso or $C_4H_9$-sec and R is $CH_3$, $C_2H_5$, $C_3H_7$-i, $C_4H_9$-t, $(CH_3)_2CH-CH_2$ or $(CH_3)_3C-CH_2$ are:

| Comp. | $R_1$ |
|---|---|
| 7.27 | 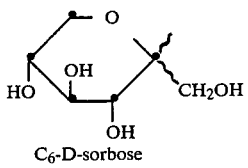 <br> $C_6$-D-sorbose |
| 7.28 | 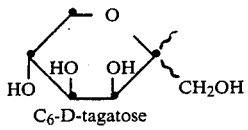 <br> $C_6$-D-tagatose |
| 7.29 | 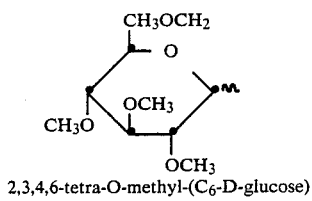 <br> 2,3,4,6-tetra-O-methyl-($C_6$-D-glucose) |
| 7.30 | 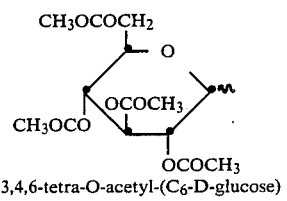 <br> 2,3,4,6-tetra-O-acetyl-($C_6$-D-glucose) |
| 7.31 | 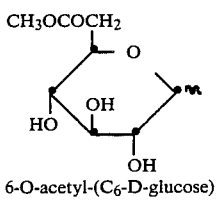 <br> 6-O-acetyl-($C_6$-D-glucose) |
| 7.32 | 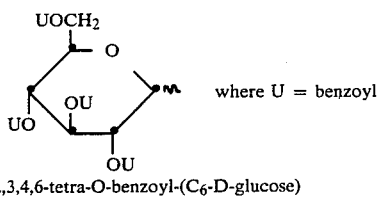 where U = benzoyl <br> 2,3,4,6-tetra-O-benzoyl-($C_6$-D-glucose) |
| 7.33 | 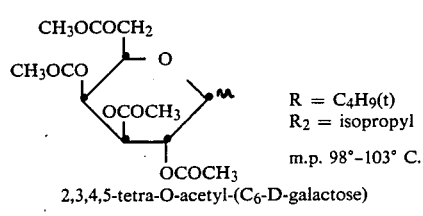 R = $C_4H_9(t)$, $R_2$ = isopropyl, m.p. 98°–103° C. <br> 2,3,4,5-tetra-O-acetyl-($C_6$-D-galactose) |

TABLE 7-continued

Typical representatives of compounds of formula I wherein $R_1$ is the group

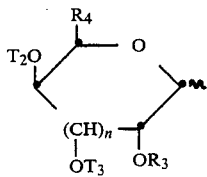

and $R_2$ is $CH_3$, $C_2H_5$, $C_3H_7$-iso or $C_4H_9$-sec and R is $CH_3$, $C_2H_5$, $C_3H_7$-i, $C_4H_9$-t, $(CH_3)_2CH-CH_2$ or $(CH_3)_3C-CH_2$ are:

| Comp. | $R_1$ |
|---|---|
| 7.34 | 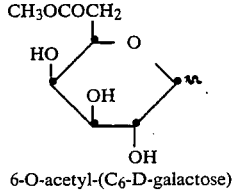 <br> 6-O-acetyl-($C_6$-D-galactose) |
| 7.35 | 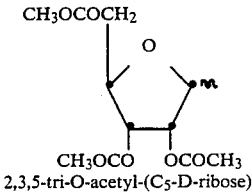 <br> 2,3,5-tri-O-acetyl-($C_5$-D-ribose) |
| 7.36 | 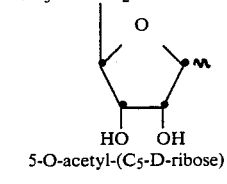 <br> 5-O-acetyl-($C_5$-D-ribose) |
| 7.37 | 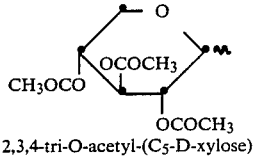 <br> 2,3,4-tri-O-acetyl-($C_5$-D-xylose) |
| 7.38 | 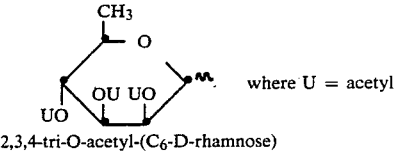 where U = acetyl <br> 2,3,4-tri-O-acetyl-($C_6$-D-rhamnose) |

TABLE 8

Typical representatives of compounds of formula I wherein X is —C(O)—:

| Comp. | $R_2$ | R | Physical data m.p. [°C.] |
|---|---|---|---|
| 8.1 | $CH_3$ | H | |
| 8.2 | $C_2H_5$ | H | |
| 8.3 | $C_3H_7$-iso | H | |
| 8.4 | $C_4H_9$-sec | H | |
| 8.5 | $CH_3$ | $CH_3$ | |
| 8.6 | $C_2H_5$ | $CH_3$ | |
| 8.7 | $C_3H_7$-iso | $CH_3$ | |
| 8.8 | $C_4H_9$-sec | $CH_3$ | |
| 8.9 | $CH_3$ | $C(CH_3)_3$ | |

TABLE 8-continued

Typical representatives of compounds of formula I wherein X is —C(O)—:

| Comp. | R₂ | R | Physical data m.p. [°C.] |
|---|---|---|---|
| 8.10 | C₂H₅ | C(CH₃)₃ | 120–123 |
| 8.11 | C₃H₇-iso | C(CH₃)₃ | |
| 8.12 | C₄H₉-sec | C(CH₃)₃ | |
| 8.13 | CH₃ | CH₃OCH₂ | |
| 8.14 | C₂H₅ | CH₃OCH₂ | |
| 8.15 | C₃H₇-iso | CH₃OCH₂ | |
| 8.16 | C₄H₉-sec | CH₃OCH₂ | |
| 8.17 | CH₃ | CH₃O(CH₃)₂C | |
| 8.18 | C₂H₅ | CH₃O(CH₃)₂C | |
| 8.19 | C₃H₇-iso | CH₃O(CH₃)₂C | |
| 8.20 | C₄H₉-sec | CH₃O(CH₃)₂C | |
| 8.21 | CH₃ | (CH₃)₂CH—CH₂ | |
| 8.22 | C₂H₅ | (CH₃)₂CH—CH₂ | |
| 8.23 | C₃H₇-iso | (CH₃)₂CH—CH₂ | |
| 8.24 | C₄H₉-sec | (CH₃)₂CH—CH₂ | |
| 8.25 | CH₃ | CCl₃ | |
| 8.26 | C₂H₅ | CCl₃ | |
| 8.27 | C₃H₇-iso | CCl₃ | |
| 8.28 | C₄H₉-sec | CCl₃ | |
| 8.29 | CH₃ | CF₃ | |
| 8.30 | C₂H₅ | CF₃ | |
| 8.31 | C₃H₇-iso | CF₃ | |
| 8.32 | C₄H₉-sec | CF₃ | |
| 8.33 | CH₃ | Cl₃CCHCl | |
| 8.34 | C₂H₅ | Cl₃CCHCl | |
| 8.35 | C₃H₇-iso | Cl₃CCHCl | |
| 8.36 | C₄H₉-sec | Cl₃CCHCl | |
| 8.37 | CH₃ | ClCH₂CH₂CH₂ | |
| 8.38 | C₂H₅ | ClCH₂CH₂CH₂ | |
| 8.39 | C₃H₇-iso | ClCH₂CH₂CH₂ | |
| 8.40 | C₄H₉-sec | ClCH₂CH₂CH₂ | |
| 8.41 | CH₃ | CH₂=CH | |
| 8.42 | C₂H₅ | CH₂=CH | |
| 8.43 | C₃H₇-iso | CH₂=CH | |
| 8.44 | C₄H₉-sec | CH₂=CH | |
| 8.45 | CH₃ | CH₂=CH—CH₂ | |
| 8.46 | C₂H₅ | CH₂=CH—CH₂ | |
| 8.47 | C₃H₇-iso | CH₂=CH—CH₂ | |
| 8.48 | C₄H₉-sec | CH₂=CH—CH₂ | |
| 8.49 | CH₃ | CH=C—CH₂ | |
| 8.50 | C₂H₅ | CH=C—CH₂ | |
| 8.51 | C₃H₇-iso | CH=C—CH₂ | |
| 8.52 | C₄H₉-sec | CH=C—CH₂ | |
| 8.53 | CH₃ | (CH₃)₂C=CH | |
| 8.54 | C₂H₅ | (CH₃)₂C=CH | |
| 8.55 | C₃H₇-iso | (CH₃)₂C=CH | |
| 8.56 | C₄H₉-sec | (CH₃)₂C=CH | |
| 8.57 | CH₃ | (Cl)₂C=C(Cl) | |
| 8.58 | C₂H₅ | (Cl)₂C=C(Cl) | |
| 8.59 | C₃H₇-iso | (Cl)₂C=C(Cl) | |
| 8.60 | C₄H₉-sec | (Cl)₂C=C(Cl) | |
| 8.61 | CH₃ | CF₃CCl₂ | |
| 8.62 | C₂H₅ | CF₃CCl₂ | |
| 8.63 | C₃H₇-iso | CF₃CCl₂ | |
| 8.64 | C₄H₉-sec | CF₃CCl₂ | |
| 8.65 | CH₃ | cyclopropyl | |
| 8.66 | C₂H₅ | cyclopropyl | |
| 8.67 | C₃H₇-iso | cyclopropyl | |
| 8.68 | C₄H₉-sec | cyclopropyl | |
| 8.69 | CH₃ | 2,2-dimethyl-cyclopropyl | |
| 8.70 | C₂H₅ | 2,2-dimethyl-cyclopropyl | |
| 8.71 | C₃H₇-iso | 2,2-dimethyl-cyclopropyl | |
| 8.72 | C₄H₉-sec | 2,2-dimethyl-cyclopropyl | |
| 8.73 | CH₃ | 2,2-dimethyl-3-(2,2-dichlorovinyl)cyclopropyl | |
| 8.74 | C₂H₅ | 2,2-dimethyl-3-(2,2-dichlorovinyl)cyclopropyl | |
| 8.75 | C₃H₇-iso | 2,2-dimethyl-3-(2,2-dichlorovinyl)cyclopropyl | |
| 8.76 | C₄H₉-sec | 2,2-dimethyl-3-(2,2-dichlorovinyl)cyclopropyl | |
| 8.77 | CH₃ | cyclobutyl | |
| 8.78 | C₂H₅ | cyclobutyl | |
| 8.79 | C₃H₇-iso | cyclobutyl | |
| 8.80 | C₄H₉-sec | cyclobutyl | |
| 8.81 | CH₃ | cyclohexyl | |
| 8.82 | C₂H₅ | cyclohexyl | |
| 8.83 | C₃H₇-iso | cyclohexyl | |
| 8.84 | C₄H₉-sec | cyclohexyl | |
| 8.85 | CH₃ | phenyl | |
| 8.86 | C₂H₅ | phenyl | |
| 8.87 | C₃H₇-iso | phenyl | |
| 8.88 | C₄H₉-sec | phenyl | |
| 8.89 | CH₃ | p-chlorophenyl | |
| 8.90 | C₂H₅ | p-chlorophenyl | |
| 8.91 | C₃H₇-iso | p-chlorophenyl | |
| 8.92 | C₄H₉-sec | p-chlorophenyl | |
| 8.93 | CH₃ | p-tolyl | |
| 8.94 | C₂H₅ | p-toyl | |
| 8.95 | C₃H₇-iso | p-tolyl | |
| 8.96 | CH₄H₉-sec | p-tolyl | |
| 8.97 | CH₃ | p-nitrophenyl | |
| 8.98 | C₂H₅ | p-nitrophenyl | |
| 8.99 | C₃H₇-iso | p-nitrophenyl | |
| 8.100 | C₄H₉-sec | p-nitrophenyl | |
| 8.101 | CH₃ | (CH₃)₃C—CH₂ | |
| 8.102 | C₂H₅ | (CH₃)₃C—CH₂ | |
| 8.103 | C₃H₇iso | (CH₃)₃C—CH₂ | |
| 8.104 | CH₄H₉-sec | (CH₃)₃C—CH₂ | |
| 8.105 | CH₃ | m-chlorophenyl | |
| 8.106 | C₂H₅ | m-chlorophenyl | |
| 8.107 | C₃H₇-iso | m-chlorophenyl | |
| 8.108 | CH₄H₉-sec | m-chlorophenyl | |
| 8.109 | CH₃ | p-methoxyphenyl | |
| 8.110 | C₂H₅ | p-methoxyphenyl | |
| 8.111 | C₃H₇-iso | p-methoxyphenyl | |
| 8.112 | CH₄H₉-sec | p-methoxyphenyl | |
| 8.113 | CH₃ | 2,6-difluorophenyl | |
| 8.114 | C₂H₅ | 2,6-difluorophenyl | |
| 8.115 | C₃H₇-iso | 2,6-difluorophenyl | |
| 8.116 | CH₄H₉-sec | 2,6-difluorophenyl | |

The contents of this Table are of illustrative nature and constitute no limitation.

TABLE 9

Typical representatives of compounds of formula 1 wherein X is —C(=N—OH)—:

| Comp. | R₂ | R | Physical data m.p. [°C.] |
|---|---|---|---|
| 9.1 | CH₃ | H | |
| 9.2 | C₂H₅ | H | |
| 9.3 | C₃H₇-iso | H | |
| 9.4 | C₄H₉-sec | H | |
| 9.5 | CH₃ | CH₃ | |
| 9.6 | C₂H₅ | CH₃ | |
| 9.7 | C₃H₇-iso | CH₃ | |
| 9.8 | C₄H₉-sec | CH₃ | |
| 9.9 | CH₃ | C(CH₃)₃ | |
| 9.10 | C₂H₅ | C(CH₃)₃ | 145–150 |
| 9.11 | C₃H₇-iso | C(CH₃)₃ | |
| 9.12 | C₄H₉-sec | C(CH₃)₃ | |
| 9.13 | CH₃ | CH₃OCH₂ | |
| 9.14 | C₂H₅ | CH₃OCH₂ | |
| 9.15 | C₃H₇-iso | CH₃OCH₂ | |
| 9.16 | C₄H₉-sec | CH₃OCH₂ | |
| 9.17 | CH₃ | CH₃O(CH₃)₂C | |
| 9.18 | C₂H₅ | CH₃O(CH₃)₂C | |
| 9.19 | C₃H₇-iso | CH₃O(CH₃)₂C | |
| 9.20 | C₄H₉-sec | CH₃O(CH₃)₂C | |
| 9.21 | CH₃ | (CH₃)₂CH—CH₂ | |
| 9.22 | C₂H₅ | (CH₃)₂CH—CH₂ | |
| 9.23 | C₃H₇-iso | (CH₃)₂CH—CH₂ | |
| 9.24 | C₄H₉-sec | (CH₃)₂CH—CH₂ | |
| 9.25 | CH₃ | CCl₃ | |
| 9.26 | C₂H₅ | CCl₃ | |
| 9.27 | C₃H₇-iso | CCl₃ | |
| 9.28 | C₄H₉-sec | CCl₃ | |

TABLE 9-continued

Typical representatives of compounds of formula 1 wherein X is —C(=N—OH)—:

| Comp. | $R_2$ | R | Physical data m.p. [°C.] |
|---|---|---|---|
| 9.29 | $CH_3$ | $CF_3$ | |
| 9.30 | $C_2H_5$ | $CF_3$ | |
| 9.31 | $C_3H_7$-iso | $CF_3$ | |
| 9.32 | $C_4H_9$-sec | $CF_3$ | |
| 9.33 | $CH_3$ | $Cl_3CCHCl$ | |
| 9.34 | $C_2H_5$ | $Cl_3CCHCl$ | |
| 9.35 | $C_3H_7$-iso | $Cl_3CCHCl$ | |
| 9.36 | $C_4H_9$-sec | $Cl_3CCHCl$ | |
| 9.37 | $CH_3$ | $ClCH_2CH_2CH_2$ | |
| 9.38 | $C_2H_5$ | $ClCH_2CH_2CH_2$ | |
| 9.39 | $C_3H_7$-iso | $ClCH_2CH_2CH_2$ | |
| 9.40 | $C_4H_9$-sec | $ClCH_2CH_2CH_2$ | |
| 9.41 | $CH_3$ | $CH_2=CH$ | |
| 9.42 | $C_2H_5$ | $CH_2=CH$ | |
| 9.43 | $C_3H_7$-iso | $CH_2=CH$ | |
| 9.44 | $C_4H_9$-sec | $CH_2=CH$ | |
| 9.45 | $CH_3$ | $CH_2=CH—CH_2$ | |
| 9.46 | $C_2H_5$ | $CH_2=CH—CH_2$ | |
| 9.47 | $C_3H_7$-iso | $CH_2=CH—CH_2$ | |
| 9.48 | $C_4H_9$-sec | $CH_2=CH—CH_2$ | |
| 9.49 | $CH_3$ | $CH\equiv C—CH_2$ | |
| 9.50 | $C_2H_5$ | $CH\equiv C—CH_2$ | |
| 9.51 | $C_3H_7$-iso | $CH\equiv C—CH_2$ | |
| 9.52 | $C_4H_9$-sec | $CH\equiv C—CH_2$ | |
| 9.53 | $CH_3$ | $(CH_3)_2C=CH$ | |
| 9.54 | $C_2H_5$ | $(CH_3)_2C=CH$ | |
| 9.55 | $C_3H_7$-iso | $(CH_3)_2C=CH$ | |
| 9.56 | $C_4H_9$-sec | $(CH_3)_2C=CH$ | |
| 9.57 | $CH_3$ | $(Cl)_2C=C(Cl)$ | |
| 9.58 | $C_2H_5$ | $(Cl)_2C=C(Cl)$ | |
| 9.59 | $C_3H_7$-iso | $(Cl)_2C=C(Cl)$ | |
| 9.60 | $C_4H_9$-sec | $(Cl)_2C=C(Cl)$ | |
| 9.61 | $CH_3$ | $CF_3CCl_2$ | |
| 9.62 | $C_2H_5$ | $CF_3CCl_2$ | |
| 9.63 | $C_3H_7$-iso | $CF_3CCl_2$ | |
| 9.64 | $C_4H_9$-sec | $CF_3CCl_2$ | |
| 9.65 | $CH_3$ | cyclopropyl | |
| 9.66 | $C_2H_5$ | cyclopropyl | |
| 9.67 | $C_3H_7$-iso | cyclopropyl | |
| 9.68 | $C_4H_9$-sec | cyclopropyl | |
| 9.69 | $CH_3$ | 2,2-dimethyl-cyclopropyl | |
| 9.70 | $C_2H_5$ | 2,2-dimethyl-cyclopropyl | |
| 9.71 | $C_3H_7$-iso | 2,2-dimethyl-cyclopropyl | |
| 9.72 | $C_4H_9$-sec | 2,2-dimethyl-cyclopropyl | |
| 9.73 | $CH_3$ | 2,2-dimethyl-3-(2,2-dichlorovinyl)cyclopropyl | |
| 9.74 | $C_2H_5$ | 2,2-dimethyl-3-(2,2-dichlorovinyl)cyclopropyl | |
| 9.75 | $C_3H_7$-iso | 2,2-dimethyl-3-(2,2-dichlorovinyl)cyclopropyl | |
| 9.76 | $C_4H_9$-sec | 2,2-dimethyl-3-(2,2-dichlorovinyl)cyclopropyl | |
| 9.77 | $CH_3$ | cyclobutyl | |
| 9.78 | $C_2H_5$ | cyclobutyl | |
| 9.79 | $C_3H_7$-iso | cyclobutyl | |
| 9.80 | $C_4H_9$-sec | cyclobutyl | |
| 9.81 | $CH_3$ | cyclohexyl | |
| 9.82 | $C_2H_5$ | cyclohexyl | |
| 9.83 | $C_3H_7$-iso | cyclohexyl | |
| 9.84 | $C_4H_9$-sec | cyclohexyl | |
| 9.85 | $CH_3$ | phenyl | |
| 9.86 | $C_2H_5$ | phenyl | |
| 9.87 | $C_3H_7$-iso | phenyl | |
| 9.88 | $C_4H_9$-sec | phenyl | |
| 9.89 | $CH_3$ | p-chlorophenyl | |
| 9.90 | $C_2H_5$ | p-chlorophenyl | |
| 9.91 | $C_3H_7$-iso | p-chlorophenyl | |
| 9.92 | $C_4H_9$-sec | p-chlorophenyl | |
| 9.93 | $CH_3$ | p-tolyl | |
| 9.94 | $C_2H_5$ | p-tolyl | |
| 9.95 | $C_3H_7$-iso | p-tolyl | |
| 9.96 | $C_4H_9$-sec | p-tolyl | |
| 9.97 | $CH_3$ | p-nitrophenyl | |
| 9.98 | $C_2H_5$ | p-nitrophenyl | |
| 9.99 | $C_3H_7$-iso | p-nitrophenyl | |
| 9.100 | $C_4H_9$-sec | p-nitrophenyl | |
| 9.101 | $CH_3$ | $(CH_3)_3C—CH_2$ | |
| 9.102 | $C_2H_5$ | $(CH_3)_3C—CH_2$ | |
| 9.103 | $C_3H_7$-iso | $(CH_3)_3C—CH_2$ | |
| 9.104 | $C_4H_9$-sec | $(CH_3)_3C—CH_2$ | |
| 9.105 | $CH_3$ | m-chlorophenyl | |
| 9.106 | $C_2H_5$ | m-chlorophenyl | |
| 9.107 | $C_3H_7$-iso | m-chlorophenyl | |
| 9.108 | $C_4H_9$-sec | m-chlorophenyl | |
| 9.109 | $CH_3$ | p-methoxyphenyl | |
| 9.110 | $C_2H_5$ | p-methoxyphenyl | |
| 9.111 | $C_3H_7$-iso | p-methoxyphenyl | |
| 9.112 | $C_4H_9$-sec | p-methoxyphenyl | |
| 9.113 | $CH_3$ | 2,6-difluorophenyl | |
| 9.114 | $C_2H_5$ | 2,6-difluorophenyl | |
| 9.115 | $C_3H_7$-iso | 2,6-difluorophenyl | |
| 9.116 | $C_4H_9$-sec | 2,6-difluorophenyl | |

The contents of this Table are of illustrative nature and constitute no limitation.

Formulation Examples for active ingredients of formula I (throughout, percentages are by weight)

| Wettable powders | a | b | c |
|---|---|---|---|
| a compound of the Tables | 25% | 50% | 75% |
| sodium lignosulfonate | 5% | 5% | — |
| sodium laurylsulfate | 3% | —5% | — |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| Emulsifiable concentrate | |
|---|---|
| a compound of the Tables | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| Dusts | a | b |
|---|---|---|
| a compound of the Tables | 5% | 8% |
| talcum | 95% | — |
| kaolin | — | 92% |

Ready for use dusts are obtained by mixing the active ingredient with the carrier, and grinding the mixture in a suitable mill.

| Extruder granulate | |
|---|---|
| a compound of the Tables | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| Tablets or boluses | |
|---|---|
| I a compound of the Tables | 33.00% |
| methyl cellulose | 0.80% |
| highly dispersed silicic acid | 0.80% |
| maize starch | 8.40% |

The methyl cellulose is stirred in water and allowed to swell. Then the silicic acid is stirred in to give a homogeneous suspension. The compound of formula I and the maize starch are mixed and the aqueous suspension is added to the mix, which is kneaded to a paste. This paste is granulated through a 12M sieve and the granulate is dried.

| II crystalline lactose | 22.50% |
|---|---|
| maize starch | 17.00% |
| microcrystalline cellulose | 16.50% |
| magnesium stearate | 1.00% |

All 4 adjuvants are thoroughly mixed. Phases I and II are mixed and compressed to tablets or boluses.

If the compounds of formula I, or compositions containing them, are used for controlling endoparasitic nematodes, cestodes and trematodes in domestic animals and productive livestock, for example cattle, sheep, goats, cats and dogs, they can be administered to the animals in both single and repeated doses. Depending on the species of animal, the individual doses are preferably administered in amounts ranging from 0.1 to 10 mg/kg of body weight. A better action is often achieved by protracted administration, or lower total doses will also suffice. The compounds, or compositions containing them, can also be added to feeds and drinks. The ready-prepared feeds contain the active ingredients preferably in a concentration of 0.005 to 0.1 percent by weight. The compositions can be administered to the animals perorally in the form of solutions, emulsions, suspensions, powders, tablets, boluses or capsules.

If the physical and toxicological properties of solutions or emulsions permit it, the compounds of formula I, or compositions containing them, can also be injected into animals for example subcutaneously, administered intraruminally or applied to the bodies of the animals by the pour-on method. Administration by means of salt licks or molasses blocks is also possible.

BIOLOGICAL EXAMPLES

B1: Insecticidal Stomach Poison Action against *Spodoptera littoralis*

Potted cotton plants in the 5-leaf stage are sprayed with a solution containing 3, 12.5 or 50 ppm of the test compound in acetone/water. After the coating has dried, the plants are populated with about 30 larvae ($L_1$ stage) of *Spodoptera littoralis*. Two plants are used for each test compound and test species. The test is carried out at about 24° C. and 60% relative humidity. Evaluations and intermediate evaluations of moribund insects, larval growth and feeding damage are made after 24, 48 and 72 hours.

Complete kill was achieved after 24 hours with the compounds of formula I, e.g. compounds 5.10, 5.11, 5.22, 5.65, 5.103 and 7.33, at a concentration of 3 ppm.

B2: Action against Plant-destructive Acarids:
OP-sensitive *Tetranychus urticae*

16 hours before the start of the test, the primary leaves of bean plants (*Phaseolus vulgaris*) are infected with an infested piece of leaf from a mass culture of *Tetranychus urticae*. Upon removal of the piece of leaf, the plants infested with all stages of the mites are sprayed to drip point with a solution containing 0.4 ppm or 1.6 ppm of the test compound. The temperature in the greenhouse compartment is about 25° C.

The percentage of mobile stages (adults and nymphs) and of eggs is evaluated under a stereoscopic microscope after 7 days. Compounds of formula I, e.g. compounds 5.10, 5.11, 5.22, 5.65, 5.103 and 7.33, achieved complete kill at a concentration of 0.4 ppm.

B3: Action against $L_1$ Larvae of *Lucilia sericata*

1 ml of an aqueous suspension of test compound is mixed with 3 ml of a special larval culture medium at about 50° C. such that a homogeneous composition containing 250 ppm or 125 ppm of active ingredient is obtained. About 30 *Lucilia sericata* larvae ($L_1$) are put into each test tube containing active ingredient. A mortality count is made after 4 days. The compounds of formula I, e.g. compounds 5.11, 5.10, 5.66, 5.98, 5.102, 5.110 and 9.10, achieved complete kill at 125 ppm.

B4: Acaricidal Action against *Boophilus microplus* (Biarra Strain)

Adhesive tape is applied vertically across a PVC plate so that 10 fully replete female *Boophilus microplus* ticks (Biarra strain) can be affixed thereto with their backs, side by side, in a row. Each tick is injected from an injection needle with 1 $\mu l$ of a liquid which contains a 1:1 mixture of polyethylene glycol and acetone, in which mixture a specific amount of test compound of 1.0 $\mu g$ per tick is dissolved. Control ticks are injected with liquid containing no test compound. After this treatment, the ticks are detached from the support and kept in an insectarium under normal conditions at about 28° C. and 80% relative humidity until oviposition has taken place and the larvae have hatched from the eggs of the control ticks. The activity of the test compound is determined with the $IR_{90}$, i.e. the effective dose is determined at which 9 out of 10 female ticks (90%) even after 30 days lay eggs from which larvae are unable to hatch.

Compounds of formula I, e.g. compounds 5.10, 5.11, 5.22, 5.65, 5.103 and 7.33, achieved an $IR_{90}$ of 0.1 $\mu g$.

B5: Trial with Sheep Infected with Nematodes (*Haemonchus concortus* and *Trichostrongylus colubriformis*)

The test compound is administered in the form of a suspension with a stomach probe or by intraruminal injection to sheep which have been artificially infected with *Haemonchus concortus* and *Trichostrongylus colubriformis*. 1 to 3 animals are used for each dose. Each sheep is treated only once with a single dose of 1 mg or 0.5 mg/kg of body weight. Evaluation is made by comparing the number of worm eggs excreted in the faeces of the sheep before and after treatment.

Untreated sheep infected simultaneously and in the same manner are used as controls. In comparison with untreated and infected control groups, there is no nematode infestation (=complete reduction of the number of worm eggs in the faeces) in sheep which have been treated with one of the compounds of formula I, e.g. compound 5.10, 5.11, 5.22, 5.66, 5.102, 5.110, 5.98, 5.106, 5.6 and 7.33, at 1 mg/kg.

B6: Contact Action against *Aphis craccivora*

Pea plantlets which have been infested with all development stages of the aphid are sprayed with a solution prepared from an emulsifiable concentrate of the test compound and containing 50 ppm, 25 ppm or 12.5 ppm of active ingredient. After 3 days evaluation is made to establish whether at least 80% of the aphids are dead or have dropped from the plants. A composition is only rated as effective at this level of activity.

Compounds of formula I, e.g. compounds 5.10, 5.11, 5.22, 5.66, 5.102, 5.6, 5.98, 5.110, 5.106 and 7.33, achieved complete kill (=100%) at a concentration of 12.5 ppm.

B7: Larvicidal Action against *Aëdes aegypti*

A 0.1% solution of the test compound in acetone is pipetted onto the surface of 150 ml of water in beakers in amounts sufficient to give concentrations of 10 ppm, 3.3 ppm and 1.6 ppm. After the acetone has evaporated, 30 to 40 three-day-old larvae of *Aedes aegypti* are put into each beaker. Mortality counts are made after 1, 2 and 5 days.

In this test, the compounds of formula I, e.g. compounds 5.10, 5.11, 5.22, 5.65, 5.103, 5.98, 5.110, 5.6, 5.106 and 7.33, achieved complete kill of all larvae at a concentration of 1.6 ppm after 1 day.

What is claimed is:

1. A compound of formula I

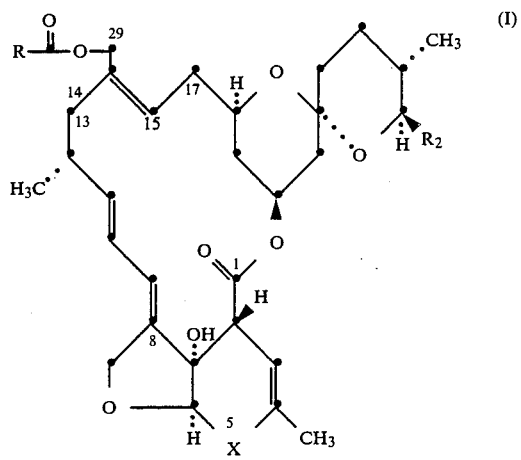

wherein
X is —CH(OR$_1$)—,
R$_1$ is hydrogen,
R$_2$ is ethyl, and
R is t-butyl.

2. A composition for controlling pests, which composition contains as an active ingredient the compound of claim 1, together with a carrier, a dispersing agent or both.

3. A method of controlling pests, which method comprises applying or administering to the host animals or applying to the host plants or to other loci of said pests a pesticidally effective amount of the compound of claim 1.

4. The method of claim 3, wherein the pests to be controlled are endoparasites or ectoparasites that attack animals.

5. The method of claim 3, wherein the pests to be controlled are plant-destructive parasites.

* * * * *